(12) United States Patent
Inoue

(10) Patent No.: US 11,559,599 B2
(45) Date of Patent: Jan. 24, 2023

(54) SCENT RETAINING STRUCTURE, METHOD OF MANUFACTURING THE SCENT RETAINING STRUCTURE, AND SCENT PROVIDING DEVICE

(71) Applicant: Sony Corporation, Tokyo (JP)

(72) Inventor: Yukito Inoue, Tokyo (JP)

(73) Assignee: Sony Corporation, Tokyo (JP)

( * ) Notice: Subject to any disclaimer, the term of this patent is extended or adjusted under 35 U.S.C. 154(b) by 14 days.

(21) Appl. No.: 16/645,130

(22) PCT Filed: Jun. 19, 2018

(86) PCT No.: PCT/JP2018/023326
§ 371 (c)(1),
(2) Date: Mar. 6, 2020

(87) PCT Pub. No.: WO2019/053989
PCT Pub. Date: Mar. 21, 2019

(65) Prior Publication Data
US 2021/0023254 A1    Jan. 28, 2021

(30) Foreign Application Priority Data
Sep. 15, 2017  (JP) .............................. JP2017-177297

(51) Int. Cl.
*A61L 9/12*    (2006.01)
(52) U.S. Cl.
CPC ......... *A61L 9/122* (2013.01); *A61L 2209/133* (2013.01)
(58) Field of Classification Search
None
See application file for complete search history.

(56) References Cited

U.S. PATENT DOCUMENTS

| 3,747,902 A | 7/1973 | Bailey |
| 2005/0001337 A1 | 1/2005 | Pankhurst et al. |

(Continued)

FOREIGN PATENT DOCUMENTS

| DE | 102008032883 A1 | 1/2010 |
| JP | S61195043 U | 12/1986 |

(Continued)

OTHER PUBLICATIONS

JP3043595U—translated document (Year: 1997).*

(Continued)

*Primary Examiner* — Jelitza M Perez
(74) *Attorney, Agent, or Firm* — K&L Gates LLP

(57) ABSTRACT

The present disclosure provides a perfume retaining structure, a method of manufacturing the perfume retaining structure, and a scent providing device that can reduce ventilation resistance of air that passes through a space in which a perfume retainer is arranged.

The perfume retaining structure includes the perfume retainer, a retaining space in which the perfume retainer is arranged, and a first opening and a second opening that allow the retaining space to be opened to the outside. The retaining space has a ventilation area that faces the first opening and the second opening, and a retaining area that is arranged adjacent to the ventilation area and communicates with the ventilation area, and the perfume retainer is arranged in the retaining area.

15 Claims, 25 Drawing Sheets

(56) References Cited

U.S. PATENT DOCUMENTS

| | | |
|---|---|---|
| 2005/0244307 A1 | 11/2005 | Gygax |
| 2010/0243754 A1 | 9/2010 | Harris |
| 2018/0303964 A1 | 10/2018 | Nomoto et al. |

FOREIGN PATENT DOCUMENTS

| | | | |
|---|---|---|---|
| JP | 63100048 | | 6/1988 |
| JP | H045964 A | | 1/1992 |
| JP | 3043595 U | * | 11/1997 |
| JP | 3043595 U | | 11/1997 |
| JP | 2013094436 A | * | 5/2013 |
| JP | 2013094436 A | | 5/2013 |
| WO | 2017068829 A1 | | 4/2017 |

OTHER PUBLICATIONS

Nakaso, N. JP2013094436A—translated document (Year: 2013).*
International Search Report for Application No. PCT/JP2018/023326, dated Sep. 25, 2018.

* cited by examiner

SCENT RETAINING STRUCTURE, METHOD OF MANUFACTURING THE SCENT RETAINING STRUCTURE, AND SCENT PROVIDING DEVICE

TECHNICAL FIELD

The present disclosure relates to a perfume retaining structure, a method of manufacturing the perfume retaining structure, and a scent providing device.

BACKGROUND ART

Technologies relating to scent providing devices that provide scents have conventionally been proposed. For example, Patent Document 1 proposes a technology for providing a scent by supplying air to a housing device that houses a perfume retainer and releasing vaporized perfume by a flow of air. Specifically, Patent Document 1 discloses a scent providing device that includes a containment portion that contains a perfume retainer, and a releasing portion that releases the scent from the perfume retainer contained in the containment portion. The scent providing device supplies air to the containment portion via a communication hole and vaporize liquid perfume retained by the perfume retainer while releasing the perfume with the air from the releasing portion.

CITATION LIST

Patent Document

Patent Document 1: Japanese Patent Application Laid-Open No. 2014-67293

SUMMARY OF THE INVENTION

Problems to be Solved by the Invention

However, in the scent providing device disclosed in Patent Document 1, an area through which air flows from the communication hole to the releasing portion and an area in which the perfume retainer is retained are not separated in the containment portion. Thus, an increase in ventilation resistance of air that passes through the containment portion is caused. Thus, there is a possibility that the flow velocity of the air that passes through the containment portion decreases and the flow rate of the released scent decreases.

Thus, the present disclosure provides a new and improved perfume retaining structure, a method of manufacturing the perfume retaining structure, and a scent providing device that can reduce the ventilation resistance of air that passes through a space in which a perfume retainer is arranged.

Solutions to Problems

The present disclosure provides a perfume retaining structure that includes a perfume retainer, a retaining space in which the perfume retainer is arranged, and a first opening and a second opening that allow the retaining space to be opened to the outside. The retaining space has a ventilation area that faces the first opening and the second opening, and a retaining area that is arranged adjacent to the ventilation area and communicates with the ventilation area, and the perfume retainer is arranged in the retaining area.

Furthermore, the present disclosure provides a method of manufacturing the perfume retaining structure, including: producing a first case body provided with the retaining space that has the ventilation area provided with the first opening, and the retaining area that is divided from the ventilation area by a first rib, arranged adjacent to the ventilation area, and communicates with the ventilation area; storing the perfume retainer or a base material of the perfume retainer in the retaining area in the first case body; producing a case by attaching, to the first case body, a second case body that has a communication hole that communicates with the retaining space in the first case body and a second rib that is erected in the retaining space in the first case body, the first rib and the second rib limiting movement of the perfume retainer toward the ventilation area; and attaching, to the case, a case cover that has the second opening.

Furthermore, the present disclosure provides a scent providing device including: the perfume retaining structure that has the perfume retainer, the retaining space in which the perfume retainer is arranged, and the first opening and the second opening that allow the retaining space to be opened to the outside; and an air blowing source that supplies air to the retaining space, in which the retaining space has the ventilation area faced by the first opening and the second opening, and the retaining area that is arranged adjacent to the ventilation area and communicates with the ventilation area, the perfume retainer being arranged in the retaining area.

Effects of the Invention

As described above, according to the present disclosure, it is possible to reduce the ventilation resistance of air that passes through a space in which a perfume retainer is arranged. Note that the effects described above are not necessarily restrictive. In addition to or in place of the effects described above, any of the effects described in the present specification or other effects that can be grasped from the present specification may be exerted.

MODE FOR CARRYING OUT THE INVENTION

Figure 1:
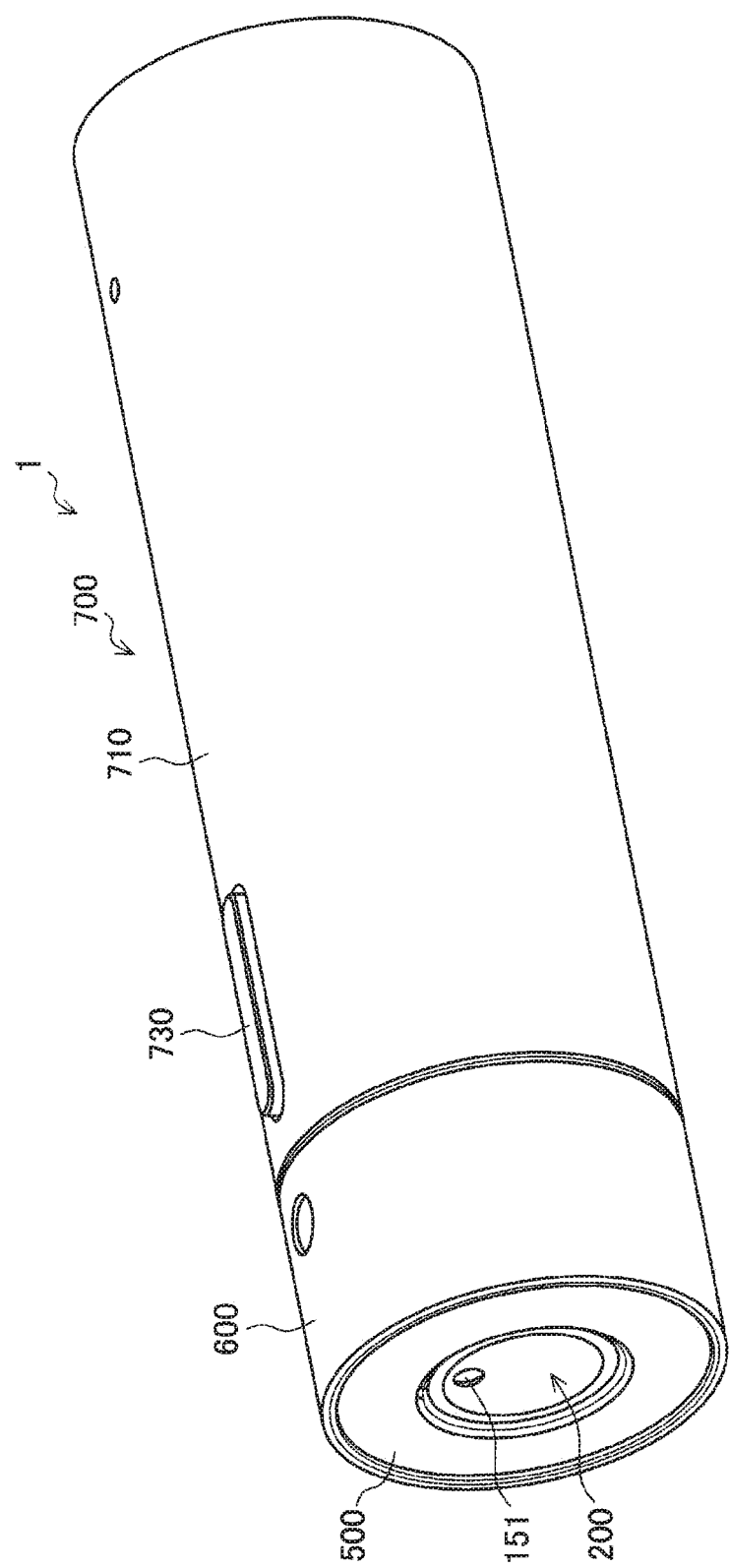
FIG. 1 is a perspective view illustrating an appearance of a scent providing device according to an embodiment of the present disclosure.

A preferred embodiment of the present disclosure will be described below in detail with reference to the accompanying drawings. Note that, in the present specification and drawings, components having substantially the same functional configurations are denoted by the same reference numerals, and the description thereof will thus not be repeated.

Note that the description will be given in the following order.

1. Outline of scent providing device
2. Configuration example of perfume cartridge (perfume retaining structure)
3. Configuration example of scent providing device
4. Method of manufacturing perfume cartridge (perfume retaining structure)

In the following description, a direction to which a scent is blown may be referred to as the front side or the front end side, and the opposite direction may be referred to as the rear side or the rear end side.

<1. Outline of Scent Providing Device>

Figure 2:
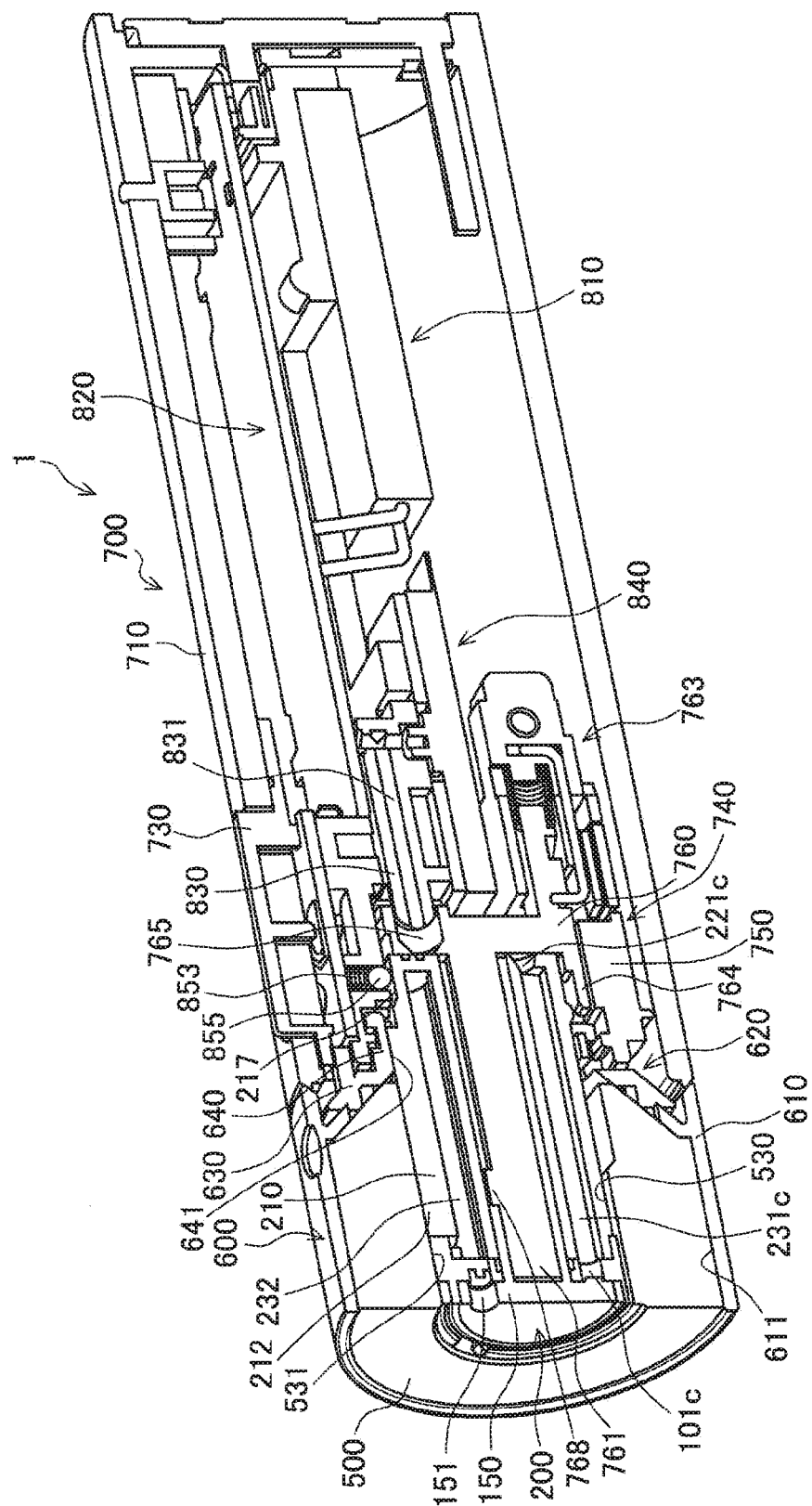
FIG. 2 is a perspective view of an axial cross section of the scent providing device according to the same embodiment.

First, a brief description will be given on an outline of a scent providing device according to the embodiment of the present disclosure. FIG. 1 is a perspective view illustrating an appearance of a scent providing device 1 according to the present embodiment. FIG. 2 is an axial sectional view of the scent providing device 1.

The scent providing device 1 according to the present embodiment includes a perfume cartridge 200 and a device main body 700. The device main body 700 has a housing 710, and the housing 710 includes a battery 810, an air pump 840, and a circuit board 820 that controls power supply from the battery 810 to the air pump 840. The perfume cartridge 200 can be attached to or detached from the front side of the device main body 700. In the present embodiment, the perfume cartridge 200 corresponds to a perfume retaining structure.

The scent providing device 1 causes air to flow into a desired retaining space 231 selected from a plurality of retaining spaces 231 (only one retaining space 231c is illustrated in FIG. 2) disposed in the perfume cartridge 200 to vaporize and release perfume retained by a perfume retainer (not illustrated) arranged in each retaining space 231. For example, the scent providing device 1 causes air supplied from the air pump 840 to pass through the retaining space 231 in the perfume cartridge 200, thereby vaporizing liquid perfume or moist perfume (hereinafter collectively referred to as "liquid perfume") and releasing the perfume, together with air, from the retaining space 231.

The scent providing device 1 according to the present embodiment is used as, for example, a device for releasing a scent into a limited range of space. For example, a user releases the scent from the scent providing device 1 once or a plurality of times near the user's face to get relaxed. In this case, the scent providing device 1 releases the scent in a straight direction to prevent the scent from spreading widely, and this prevents the scent to be perceived by people nearby. The scent providing device 1 may be a portable device that can be carried by a user or may be a stationary device.

<2. Perfume Cartridge (Perfume Retaining Structure)>

Next, the perfume cartridge 200 as the perfume retaining structure according to the present embodiment will be described in detail.

Figure 3:
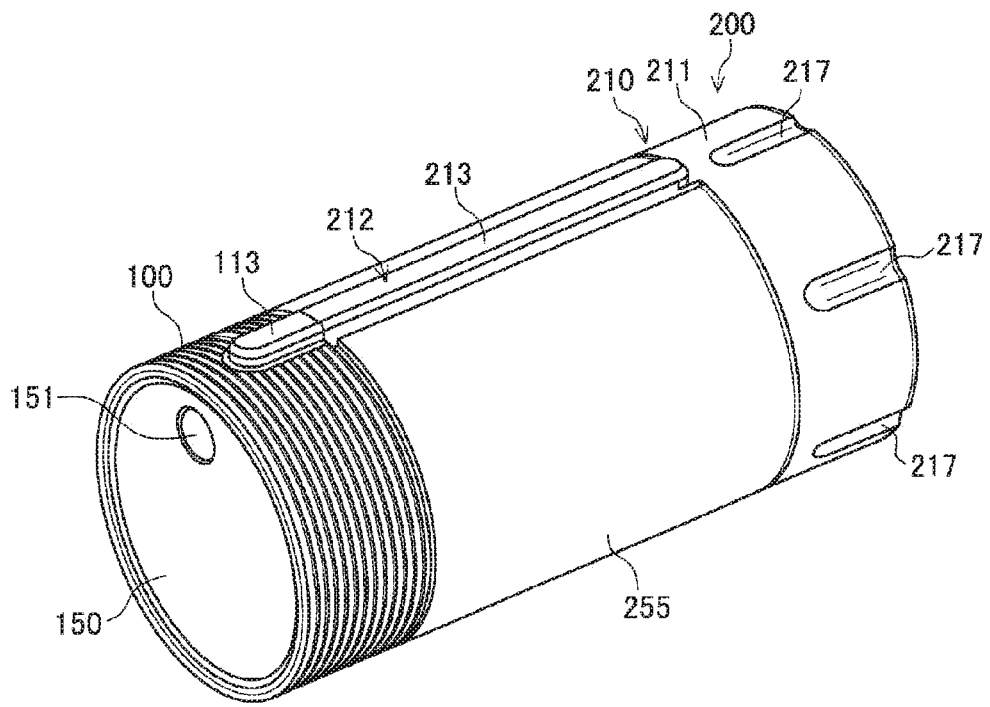
FIG. 3 is a perspective view illustrating an appearance of a perfume retaining structure according to the same embodiment.

FIGS. 3 to 7 are views for describing a configuration example of the perfume cartridge 200. FIG. 3 is a perspective view illustrating an appearance of the perfume cartridge

Figure 4:
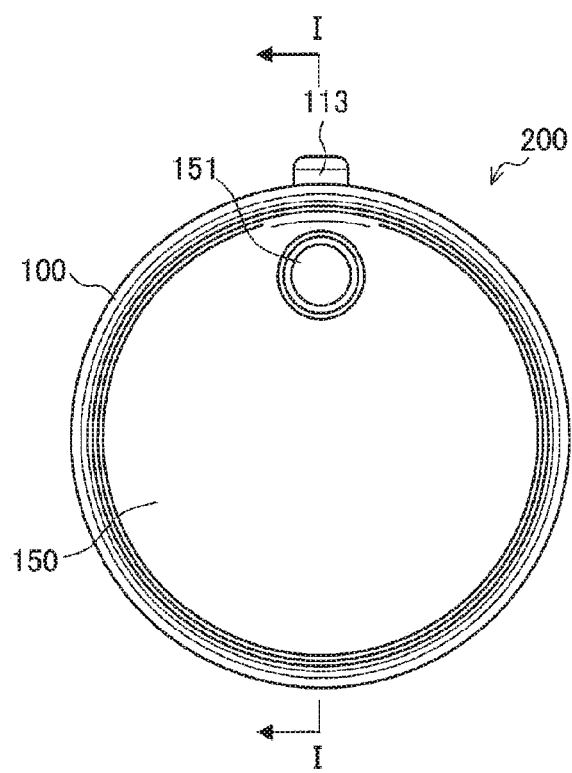
FIG. 4 is a front view of the perfume retaining structure according to the same embodiment as viewed in the axial direction.
Figure 5:
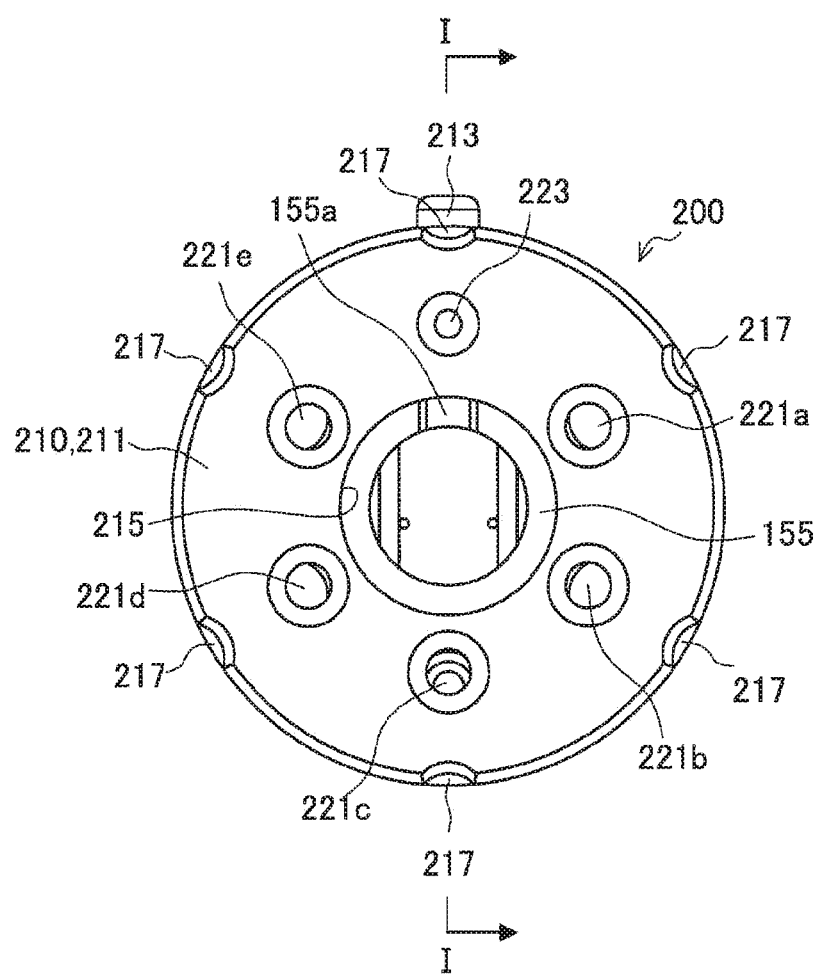
FIG. 5 is a rear view of the perfume retaining structure according to the same embodiment as viewed in the axial direction.
Figure 6:
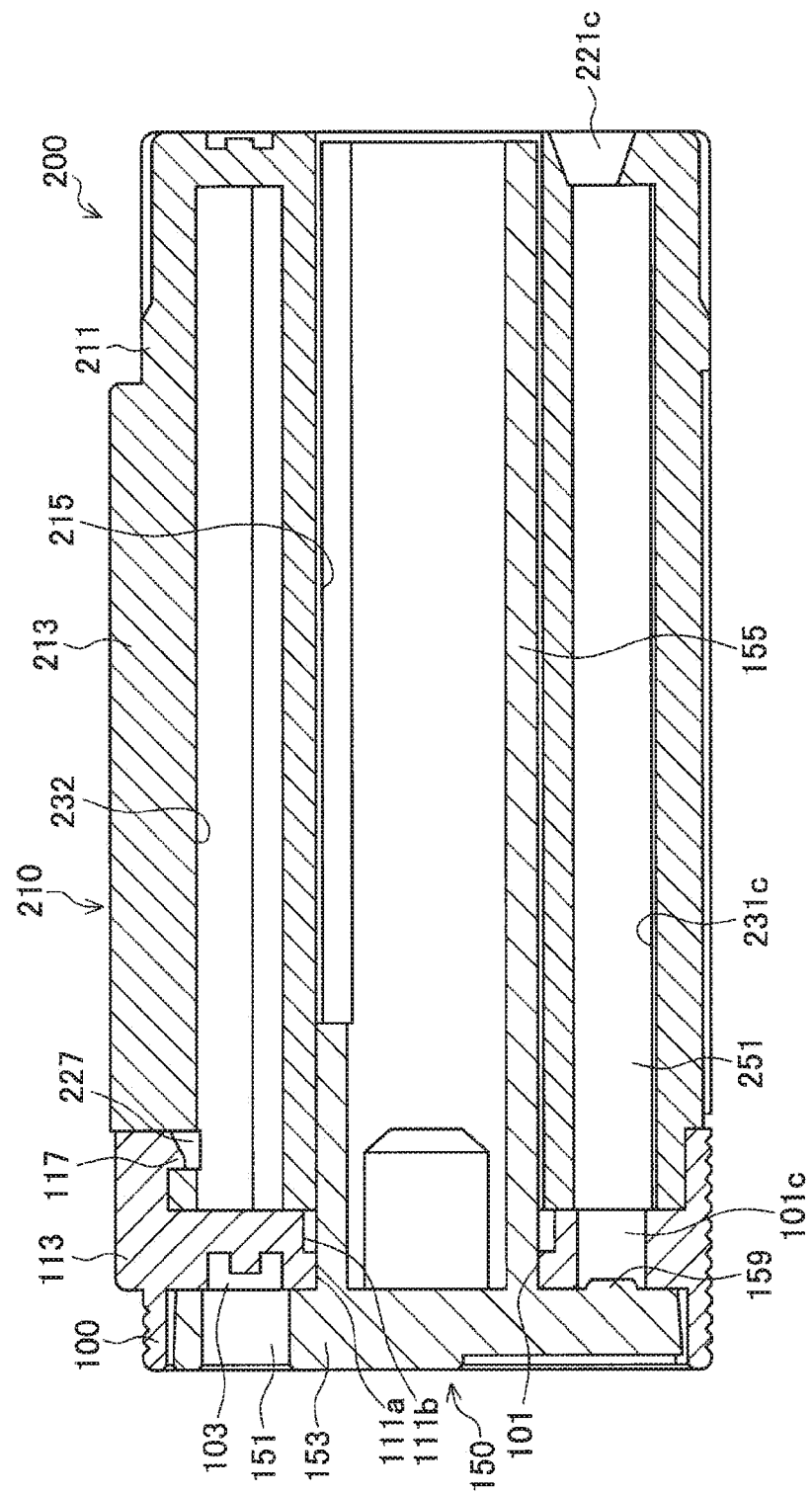
FIG. 6 is an axial sectional view of the perfume retaining structure according to the same embodiment.
Figure 7:
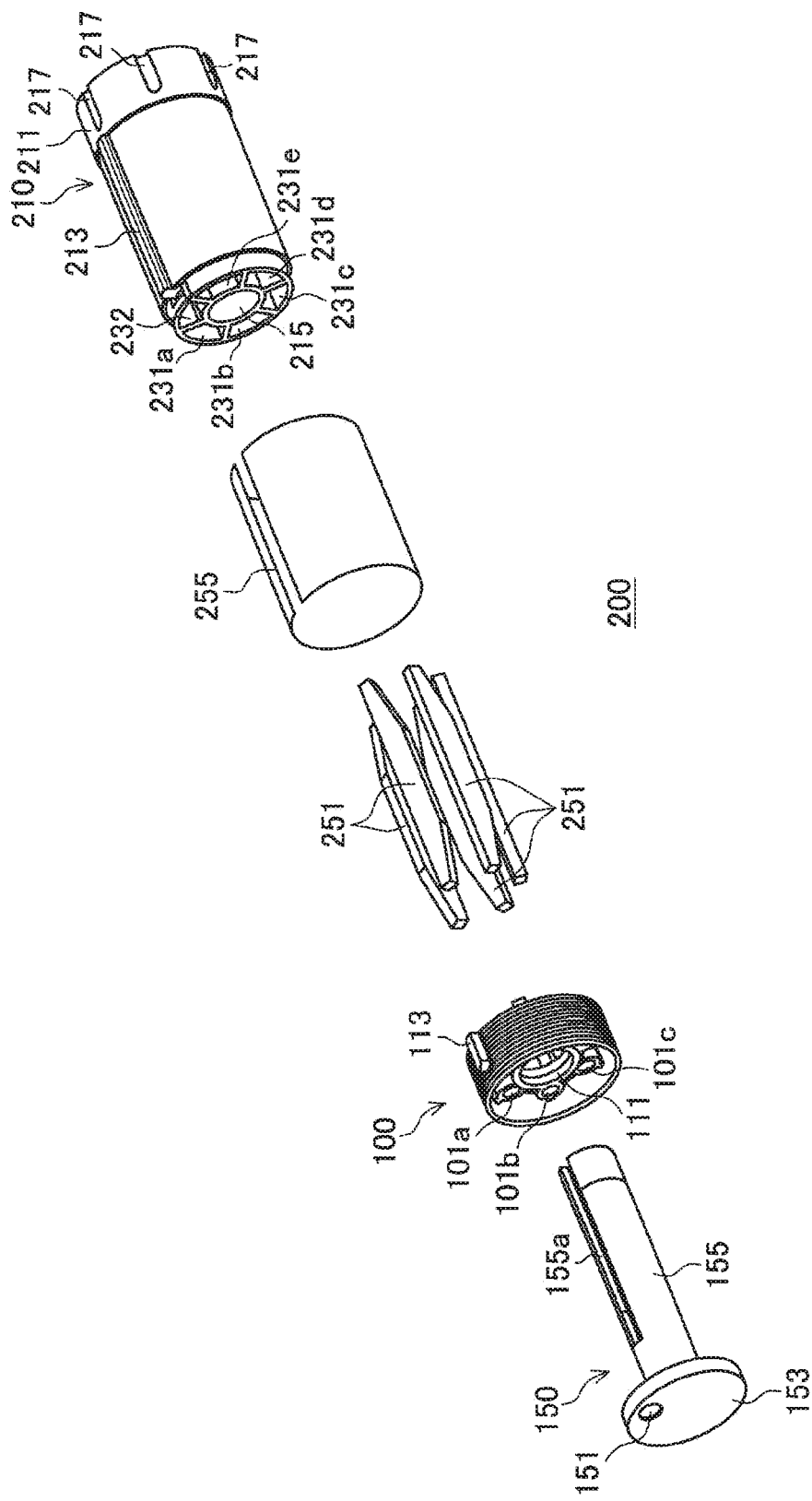
FIG. 7 is an exploded perspective view of the perfume retaining structure according to the same embodiment.

200. FIG. 4 is a front view of the perfume cartridge 200 as viewed in the axial direction from the front side. FIG. 5 is a rear view of the perfume cartridge 200 as viewed in the axial direction from the rear side. FIG. 6 is an axial sectional view of the perfume cartridge 200, and is an arrow view of a cross section taken along line I-I illustrated in FIGS. 4 and 5. FIG. 7 is an exploded perspective view of the perfume cartridge 200.

The perfume cartridge 200 has a cylindrical appearance as a whole. The perfume cartridge 200 has a plurality of (five in the present embodiment) retaining spaces 231a to 231e (hereinafter collectively referred to as the retaining spaces 231, in a case where it is not particularly necessary to distinguish between them) for air supplied from the air pump 840, which is an example of an air blowing source, to pass through. Perfume retainers 251 that retain liquid perfume are arranged in the retaining spaces 231. The perfume may be, for example, an essential oil or an essential oil diluted with ethanol. One retaining space 231 may be included, or a plurality of the retaining spaces 231 may be included.

The perfume cartridge 200 according to the present embodiment includes a case 210, a case cover 150, and the perfume retainers 251. The case 210 includes a first case body 211 and a second case body 100 fixed to the front side of the first case body 211. The case cover 150 is attached to the front surface of the case 210 so as to be axially rotatable. The perfume retainers 251 retain liquid perfume and are arranged in the corresponding plurality of retaining spaces 231 disposed in the case 210.

The perfume cartridge 200 has, on the rear end surface, first openings 221a to 221e (hereinafter collectively referred to as the first openings 221 in a case where it is not particularly necessary to distinguish between them) of the same number as the retaining spaces 231. The first openings 221 allow the corresponding retaining spaces 231 to be opened to the outside. In the present embodiment, the five first openings 221a to 221e, together with one pseudo hole 223, are arranged at regular intervals of 60 degrees around the axis. Furthermore, the perfume cartridge 200 has a second opening 151 in the front end surface. The second opening 151 is disposed in the case cover 150. The case cover 150 and the case 210 rotate relative to each other, and this allows the second opening 151 to selectively communicate with one of the plurality of retaining spaces 231.

Therefore, the case 210 of the perfume cartridge 200 can be axially rotated by a certain rotation angle to switch which retaining space 231 air should pass through. Perfumes retained in the retaining spaces 231 may be all the same, or some or all of the perfumes may be different from each other. In a case where all the retaining spaces 231 retain the same perfume, a user can enjoy a favorite scent for a long period of time. Furthermore, in a case where each retaining space 231 retains a different perfume, which scent to release can be switched by switching which retaining space 231 air can be supplied into. Thus, for example, the scent can be switched depending on mood.

In the perfume cartridge 200 according to the present embodiment, the five retaining spaces 231 are arranged at regular intervals of 60 degrees, and one space serves as a pseudo space 232. The pseudo space 232 is aligned with the second opening 151 of the case cover 150 in a case where the scent providing device 1 is not in use, so as not to let the scent escape from each retaining space 231 in the perfume cartridge 200. Note that the number of the retaining spaces 231 is not limited to five. Furthermore, the retaining spaces 231 may not be positioned at regular intervals.

The perfume cartridge 200 has, on the outer peripheral surface, a protrusion 212 that serves as a positioning element for fitting the perfume cartridge 200. The protrusion 212 is formed by a protrusion 113 of the second case body 100 and a protrusion 213 of the first case body 211 that are continuously disposed, and has a predetermined length along the axial direction.

The perfume cartridge 200 includes, on the outer peripheral surface on the rear end side, recesses 217 of the same number as the plurality of retaining spaces 231 and the pseudo space 232 combined. In the present embodiment, the plurality of recesses 217 is disposed at regular intervals of 60 degrees in the circumferential direction. The plurality of recesses 217 is disposed at positions corresponding to positions of the first openings 221 and the pseudo hole 223 disposed in the rear end surface. The recesses 217, which engage with an engagement element included in the device main body 700, have a function of fixing the case 210 at a predetermined rotation position and giving a user a rotational operation feeling. Note that the plurality of recesses 217 is only required to be disposed in the circumferential direction at the same phase intervals as the first openings 221 and the pseudo hole 223. The recesses 217 may not be disposed at regular intervals, or may not be aligned with the positions of the first openings 221 and the pseudo hole 223.

A label 255 is affixed to, excluding the protrusion 213, the outer peripheral surface of the first case body 211 positioned in a central portion in the axial direction of the perfume cartridge 200. The label 255 shows, for example, information regarding the scent of each of the perfume retainers 251 arranged in the corresponding retaining spaces 231. Note that the label 255 may not be included.

The perfume cartridge 200 will be described below in detail on a component-by-component basis.

(First Case Body)

Figure 8:
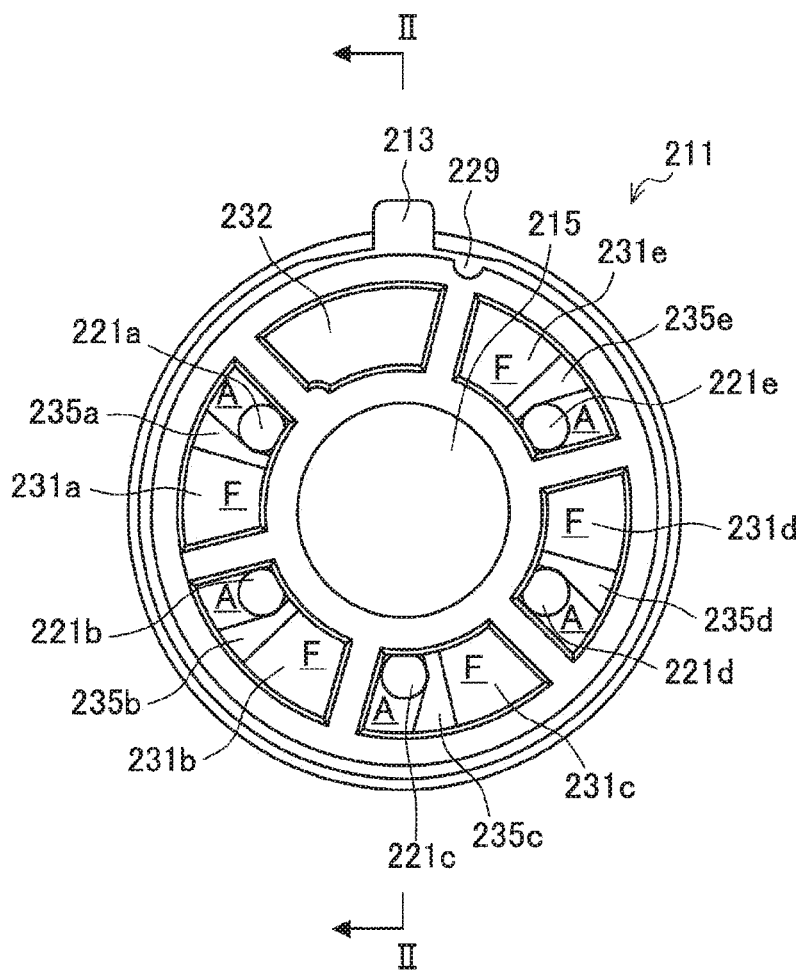
FIG. 8 is a front view of a first case body of the perfume retaining structure according to the same embodiment as viewed in the axial direction.
Figure 9:
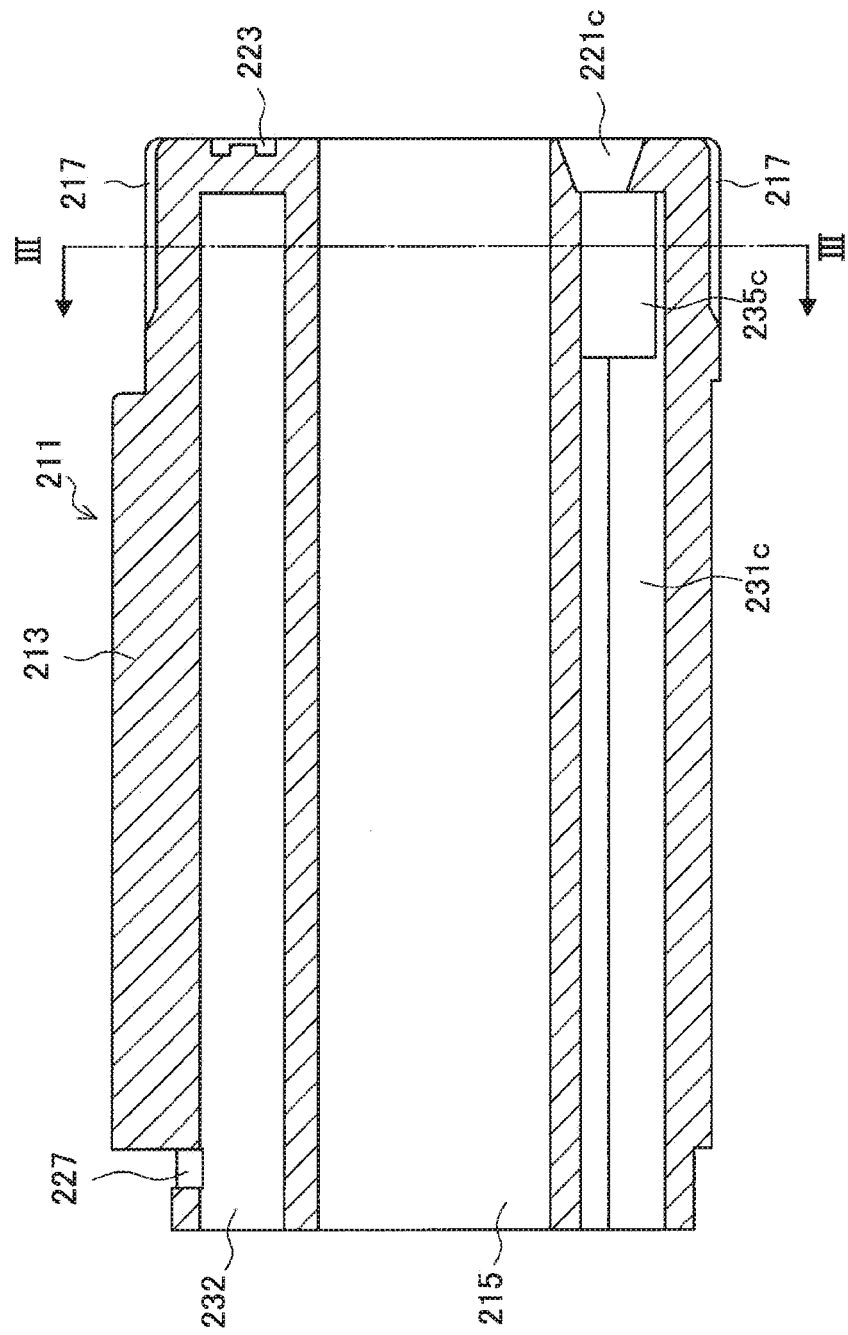
FIG. 9 is an axial sectional view of the first case body of the perfume retaining structure according to the same embodiment.
Figure 10:
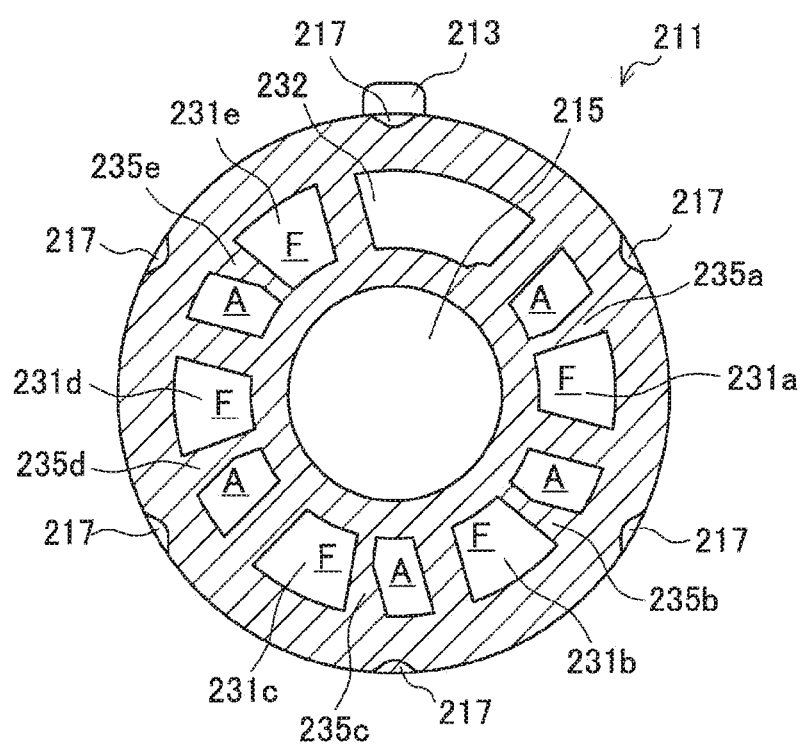
FIG. 10 is a circumferential sectional view of the first case body of the perfume retaining structure according to the same embodiment.

FIGS. 8 to 10 are views illustrated for description of the first case body 211. FIG. 8 is a front view of the first case body 211 as viewed in the axial direction from the front side. FIG. 9 is an axial sectional view of the first case body 211, and is an arrow view of a cross section taken along line II-II in FIG. 8. FIG. 10 is a circumferential sectional view of the first case body 211, and corresponds to a sectional view at line illustrated in FIG. 9. Note that a rear view of the first case body 211 as viewed in the axial direction from the rear side coincides with a rear view of the perfume cartridge 200 illustrated in FIG. 11.

The first case body 211 has a cylindrical outer shape in which the length in the axial direction is longer than the diameter. An axial hole 215 that has openings on both end sides in the axial direction is disposed in a central portion of the first case body 211. Around the axial hole 215, the plurality of (five in the present embodiment) retaining spaces 231 and the pseudo space 232 are disposed around the axis at predetermined intervals (at regular intervals of 60 degrees in the present embodiment). The plurality of retaining spaces 231 and the pseudo space 232 each has a fan-like circumferential cross-sectional shape.

The plurality of retaining spaces 231 and the pseudo space 232 each has an opening on the front side of the first case body 211. Furthermore, the rear sides of the plurality of retaining spaces 231 are opened to the outside via the corresponding first openings 221, while the rear side of the pseudo space 232 is closed. The plurality of retaining spaces 231 has first ribs 235a to 235e (hereinafter collectively referred to as the first ribs 235 in a case where it is not particularly necessary to distinguish between them) that are formed to divide a rear end portion of each retaining space 231 in the circumferential direction. In each retaining space 231, the first opening 221 is arranged on one side of areas divided in the circumferential direction by the first rib 235. Thus, the plurality of first openings 221 is also arranged at regular intervals of 60 degrees around the axis so as to correspond to the positions of the retaining spaces 231.

The protrusion 213 having a predetermined length along the axial direction is disposed on the outer peripheral surface of the first case body 211, at a position corresponding to an outer peripheral portion of the pseudo space 232. A hole 227 that communicates between the outer peripheral surface of the first case body 211 and the pseudo space 232 is disposed adjacent to the front side of the protrusion 213. The hole 227 like this, together with an engagement projection (117) of the second case body 100, has a function of fixing the first case body 211 and the second case body 100. The hole 227 may be a recess that does not reach the pseudo space 232. A plurality of the holes 227 may be disposed at different phase positions.

A recess 229 is disposed on the outer peripheral surface of a front side end portion of the first case body 211, in a portion positioned at a boundary between the pseudo space 232 and the retaining space 231e. The recess 229 like this, together with a ridge 119 of the second case body 100, has a function as a positioning element for assembling the first case body 211 and the second case body 100. The ridge may be disposed on the first case body 211, and the recess may be disposed on the second case body 100.

(Second case body)

Figure 11:
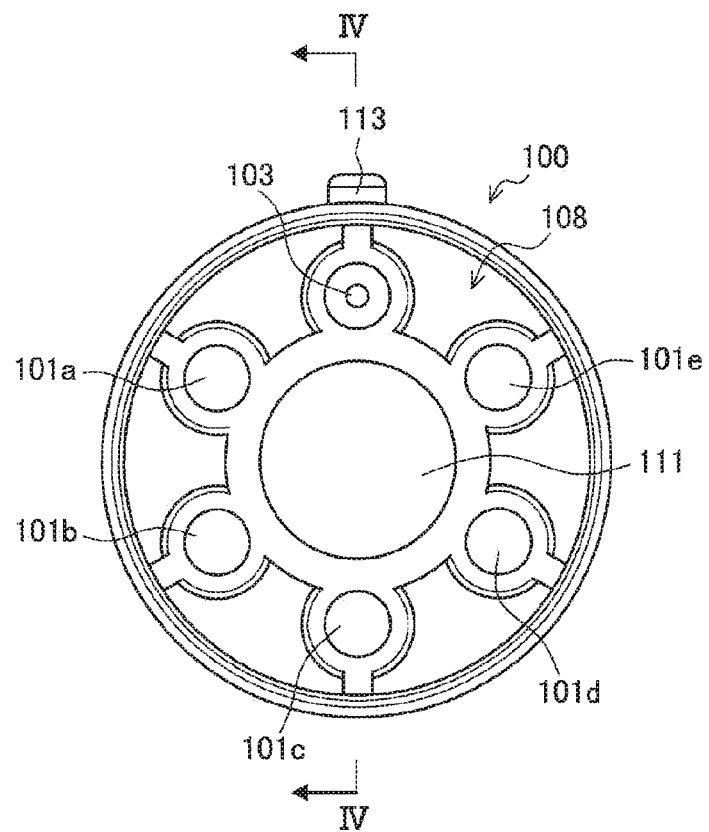
FIG. 11 is a front view of a second case body of the perfume retaining structure according to the same embodiment as viewed in the axial direction.
Figure 12:
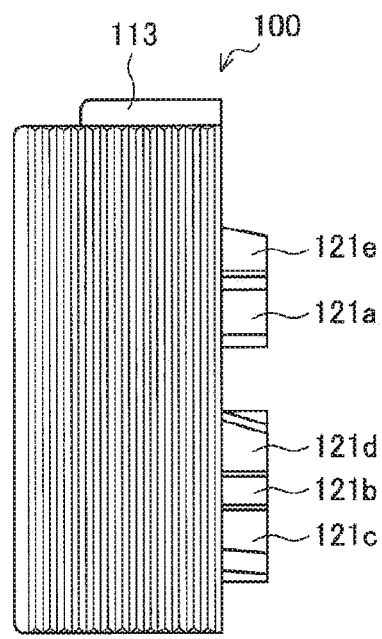
FIG. 12 is a side view of the second case body of the perfume retaining structure according to the same embodiment.
Figure 13:
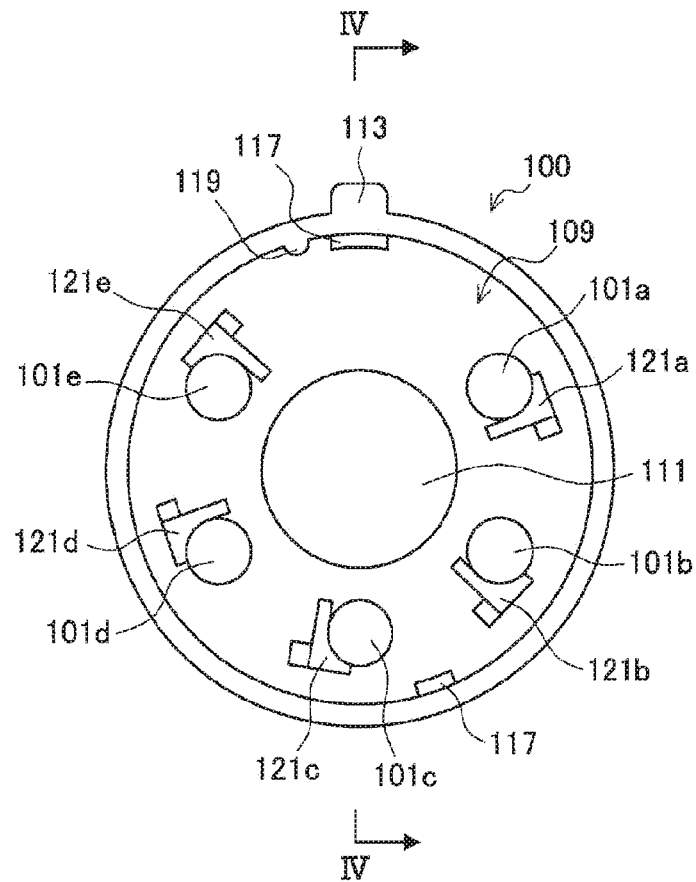
FIG. 13 is a rear view of the second case body of the perfume retaining structure according to the same embodiment as viewed in the axial direction.
Figure 14:
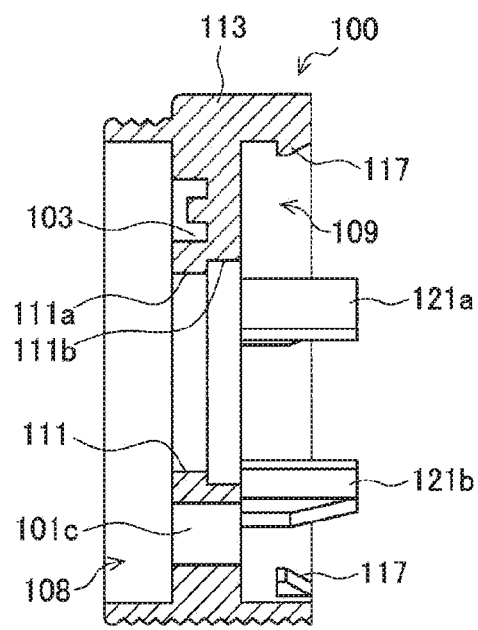
FIG. 14 is an axial sectional view of the second case body of the perfume retaining structure according to the same embodiment.

FIGS. 11 to 14 are views illustrated for description of the second case body 100. FIG. 11 is a front view of the second case body 100 as viewed in the axial direction from the front side. FIG. 12 is a side view of the second case body 100. FIG. 13 is a rear view of the second case body 100 as viewed in the axial direction from the rear side. FIG. 14 is an axial sectional view of the second case body 100, and is an arrow view of a cross section taken along line Iv-Iv in FIGS. 11 and 13.

The second case body 100 has a cylindrical outer shape in which the length in the axial direction is shorter than the diameter. The outer peripheral surface of the second case body 100 is knurled, and is provided with a plurality of fine grooves formed along the circumferential direction.

An axial hole 111 that has openings on both end sides in the axial direction is disposed in a central portion of the second case body 100. The axial hole 111 has a small-diameter portion 111a on the front side and a large-diameter portion 111b on the rear side. In a state where the second case body 100 is attached to the first case body 211, the axial hole 111 in the second case body 100 can be integrated with the axial hole 215 in the first case body 211 to form one axial hole. Around the axial hole 111, a plurality of (five in the present embodiment) communication holes 101a to 101e (hereinafter collectively referred to as the communication holes 101 in a case where it is not particularly necessary to distinguish between them) each having openings on both ends in the axial direction is disposed. The plurality of communication holes 101, together with one pseudo hole 103, is disposed around the axial hole 111 at regular intervals (at regular intervals of 60 degrees in the present embodiment). However, the communication holes 101 may not be positioned at regular intervals.

In a state where the second case body 100 is attached to the first case body 211, the plurality of communication holes 101a to 101e communicates with the retaining spaces 231a to 231e, respectively, and allows the retaining spaces 231a to 231e to be opened to the outside. The first openings 221a to 221e respectively disposed in the retaining spaces 231a to 231e and the corresponding communication holes 101a to 101e in the second case body 100 are positioned in the same phase around the axis. That is, the first opening 221 disposed in each retaining space 231 is linearly connected with the corresponding communication hole 101 along the axial direction.

On the rear end surface of the second case body 100, second ribs 121a to 121e (hereinafter collectively referred to as the second ribs 121 in a case where it is not particularly necessary to distinguish between them) are disposed adjacent to the corresponding communication holes 101a to 101e. The second ribs 121 are erected so as to extend rearward, and are arranged in the retaining spaces 231 in the second case body 100 in a state where the second case body 100 is attached to the first case body 211. Furthermore, when the state where the second case body 100 is attached to the first case body 211 is viewed in the axial direction, the second ribs 121 of the second case body 100 are arranged to overlap the first ribs 235 of the first case body 211. The second ribs 121 of the second case body 100 and the first ribs 235 of the first case body 211 divide each retaining space 231 into an area facing the communication hole 101 and the first opening 221 (ventilation area A), and the remaining area in which the perfume retainer 251 is arranged (retaining area F) (see FIGS. 8 and 10).

The second case body 100 has, on the front side, a front-side recess 108 that contains the case cover 150. Furthermore, the second case body 100 has, on the rear side, a rear-side recess 109 that contains a front end portion of the first case body 211. The engagement projection 117 that engages with the hole 227 in the first case body 211 is disposed on the inner peripheral surface of the rear-side recess 109. In the present embodiment, two engagement projections 117 are disposed (see FIGS. 13 and 14). Furthermore, the ridge 119 that is inserted into a recess 219 of the first case body 211 is disposed on the inner peripheral surface of the rear-side recess 109.

When the second case body 100 and the first case body 211 are assembled, the second case body 100 and the first case body 211 are aligned using the ridge 119 and the recess 219 and are fixed using the engagement projections 117 and the holes 227. At that time, in a state where the front end portion of the first case body 211 is fitted in the rear-side recess 109 of the second case body 100, the front end surface of the first case body 211 abuts against the bottom surface of the rear-side recess 109 of the second case body 100, and the retaining spaces 231a to 231e are isolated from one another.

The protrusion 113 having a predetermined length along the axial direction is disposed on the outer peripheral surface of the second case body 100, at a position corresponding to an outer peripheral portion in which the pseudo hole 103 is arranged. In a state where the second case body 100 is attached to the first case body 211, the protrusion 113 of the second case body 100 and the protrusion 213 of the first case body 211 are continuously arranged and integrated to form the protrusion 212.

(Case cover)

Figure 15:
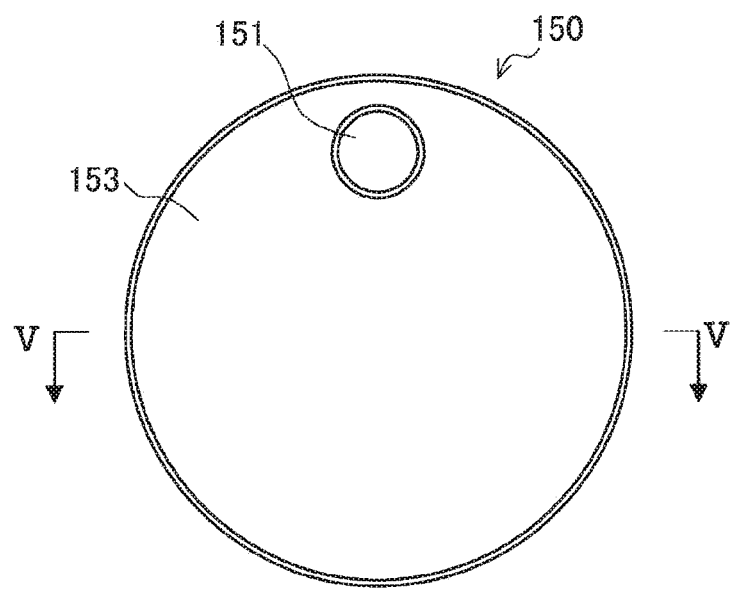
FIG. 15 is a front view of a case cover of the perfume retaining structure according to the same embodiment as viewed in the axial direction.
Figure 16:
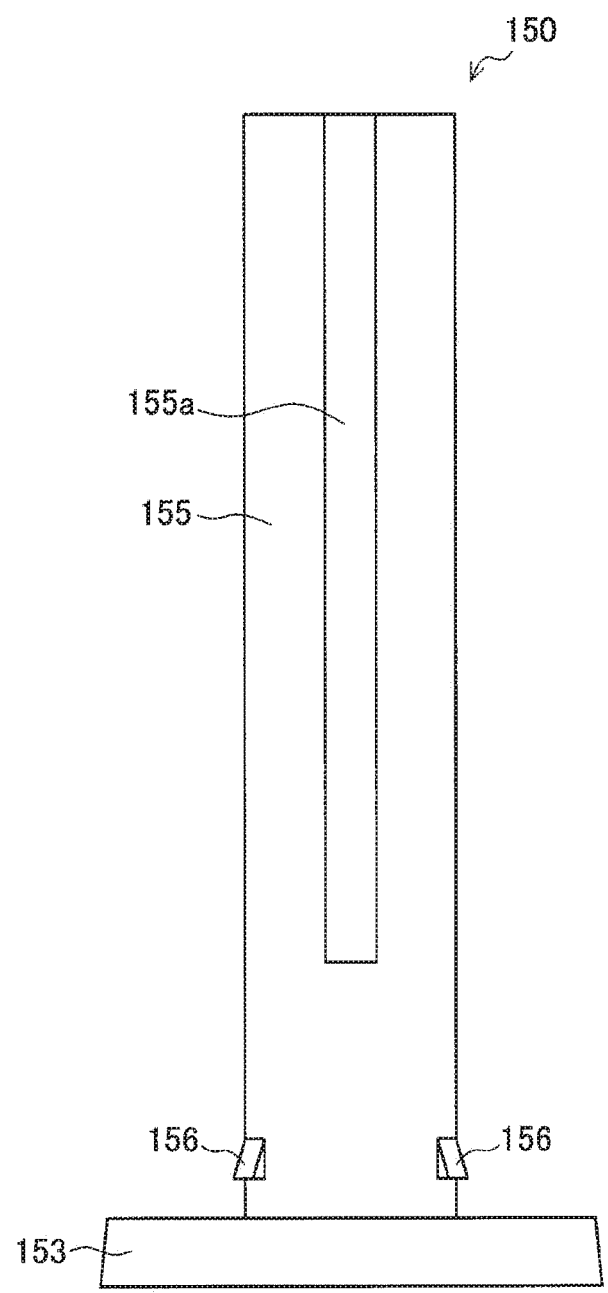
FIG. 16 is a side view of the case cover of the perfume retaining structure according to the same embodiment.
Figure 17:
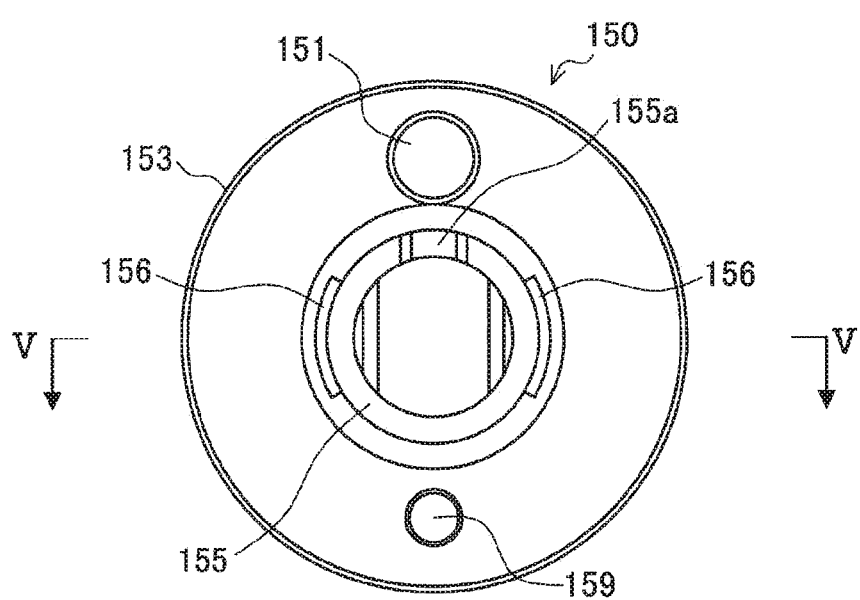
FIG. 17 is a rear view of the case cover of the perfume retaining structure according to the same embodiment as viewed in the axial direction.
Figure 18:
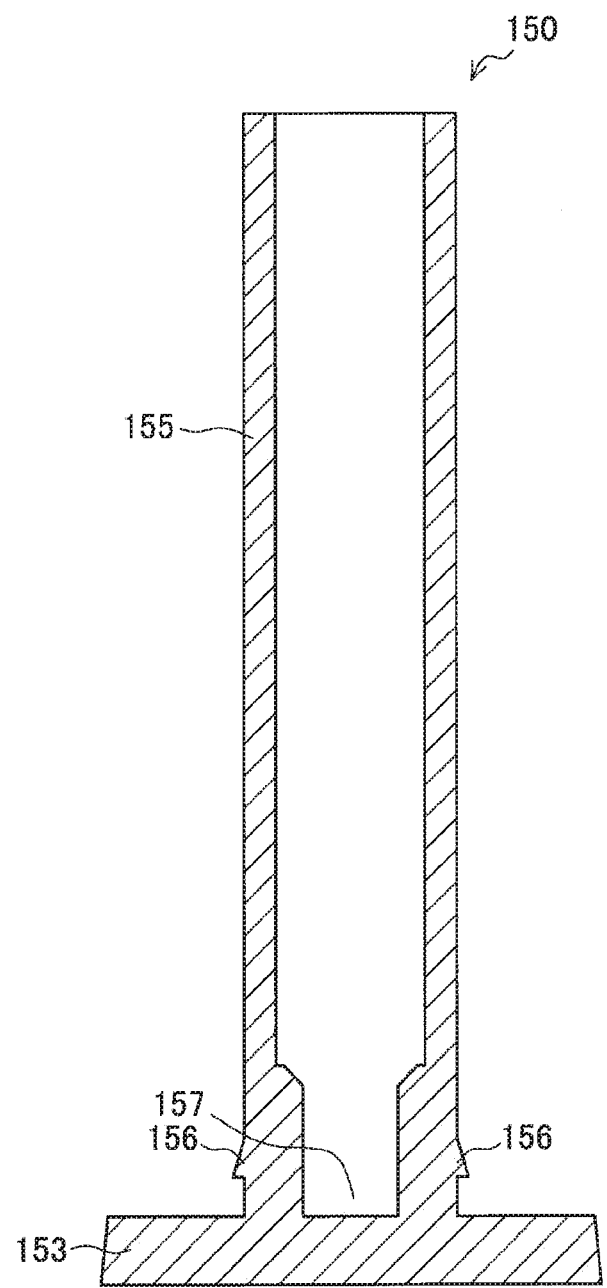
FIG. 18 is an axial sectional view of the case cover of the perfume retaining structure according to the same embodiment.

FIGS. 15 to 18 are views illustrated for description of the case cover 150. FIG. 15 is a front view of the case cover 150 as viewed in the axial direction from the front side. FIG. 16 is a side view of the case cover 150 as viewed laterally, and corresponds to a view of the case cover 150 illustrated in FIG. 15 as viewed from above. FIG. 17 is a rear view of the case cover 150 as viewed in the axial direction from the rear side. FIG. 18 is an axial sectional view of the case cover 150, and is an arrow view of a cross section taken along line V-V in FIGS. 15 and 17.

The case cover 150 has a disk portion 153 and a cylindrical portion 155 erected so as to extend rearward from the disk portion 153. The cylindrical portion 155 has a hollow cylindrical shape having an opening on the rear end side. The cylindrical portion 155 is inserted into the axial hole 111 in the second case body 100 and the axial hole 215 in the first case body 211. The disk portion 153 has a disk shape of an appropriate thickness. The disk portion 153 is contained in the front-side recess 108 of the second case body 100. The case cover 150 is attached to the case 210 so as to allow relative rotation with respect to the case 210.

The case cover 150 has the second opening 151 that penetrates the disk portion 153 in the axial direction. In accordance with the relative rotation position of the case cover 150 with respect to the case 210, the second opening 151 can communicate with one of the plurality of communication holes 101 formed in the second case body 100. That is, the second opening 151 allows one of the retaining spaces 231 to be opened to the outside in accordance with the relative rotation position of the case cover 150 with respect to the case 210. An engagement protrusion 159 that protrudes rearward is formed on the rear end surface of the disk portion 153. The engagement protrusion 159 is a minute protrusion having a height of, for example, 0.15 to 0.3 mm, and is disposed at a position where the engagement protrusion 159 can engage with the communication hole 101 in the second case body 100 (see FIG. 6).

The cylindrical portion 155 has a slit 155a that extends in the axial direction. A protrusion (a portion indicated by reference numeral 768 in FIG. 26) disposed on a fixed axle of a platform portion of the device main body 700 described later is inserted into the slit 155a. The cylindrical portion 155 has, at a bottom portion of a hollow internal space, an engagement recess 157 formed by bulging on both sides of the inner peripheral surface of the cylindrical portion 155. An engagement portion (a portion indicated by reference numeral 769 in FIGS. 26 and 27) disposed at a front end portion of the fixed axle of the platform portion of the device main body 700 is inserted into the engagement recess 157. The cylindrical portion 155 has two locking claws 156 formed in a rotationally symmetrical manner on the outer peripheral surface on the front side. In a state where the cylindrical portion 155 of the case cover 150 is inserted into the axial holes 111 and 125 in the case 210, the locking claws 156 are arranged at the large-diameter portion 111b of the axial hole 111 in the second case body 100 and are locked to a step portion between the small-diameter portion 111a and the large-diameter portion 111b (see FIG. 30). Therefore, the case cover 150 does not easily come off the case 210.

(Perfume Retainer)

The perfume retainers 251 arranged in the corresponding plurality of retaining spaces 231 each includes a base material, and the base material retains liquid perfume. For example, the perfume retainers 251 may be retainers obtained by impregnating an impregnation material as a base material with liquid perfume. In this case, for example, a porous body or a fiber body that includes polyester, nylon, felt, polyacetal, or the like may be used as the impregnation material. Furthermore, it is preferable that the impregnation material has resistance to liquid perfume. The liquid perfume may be, for example, an essential oil or an essential oil diluted with ethanol. The perfume retainers 251 may retain the same liquid perfume or different liquid perfumes for each retaining space 231.

Each perfume retainer 251 is arranged in the retaining area F in the retaining space 231 in the case 210 (see FIG. 6). The dimension in the longitudinal direction (the axial direction of the perfume cartridge 200) of the perfume retainer 251 may, for example, coincide with the length in the axial direction of the retaining area F. Furthermore, in this case, a cross-sectional shape of the perfume retainer 251 perpendicular to the longitudinal direction may approximate a circumferential cross-sectional shape of the retaining area F. That is, in a case where the perfume retainer 251 has a shape that coincides with or approximates the spatial shape of the retaining area F, the perfume retainer 251 becomes relatively large in volume, and may accordingly retain a relatively large amount of liquid perfume.

However, the shape of the perfume retainer 251 is not limited to such an example. For example, the perfume retainer 251 may have a stick shape in the form of a round bar or a square bar, or may have a trapezoidal shape formed by die-cutting a plate-like base material. The perfume retainer 251 exemplified in FIG. 7 has the same length as the length in the axial direction of the retaining area F in the retaining space 231, and is constituted by a polygonal plate material having a central portion that can be arranged close to the ventilation area A side.

(Ventilation Area and Retaining Area)

As described above, each retaining space 231 has the ventilation area A and the retaining area F. The ventilation area A has both end portions in the axial direction that can face the first opening 221 and the second opening 151. In the present embodiment, the ventilation area A of each retaining space 231 can face the second opening 151 of the case cover 150 via the corresponding communication hole 101 in the second case body 100. The retaining area F is arranged adjacent to the ventilation area A and communicates with the ventilation area A, and is an area in which the perfume retainer 251 is arranged.

The ventilation area A and the retaining area F are arranged adjacent to each other, and are divided by the first rib 235 formed on the first case body 211 on the rear side of the retaining space 231 and by the second rib 121 formed on the second case body 100 on the front side of the retaining space 231. The ventilation area A and the retaining area F communicate with each other via a space between the two ribs 121 and 235.

Figure 19:
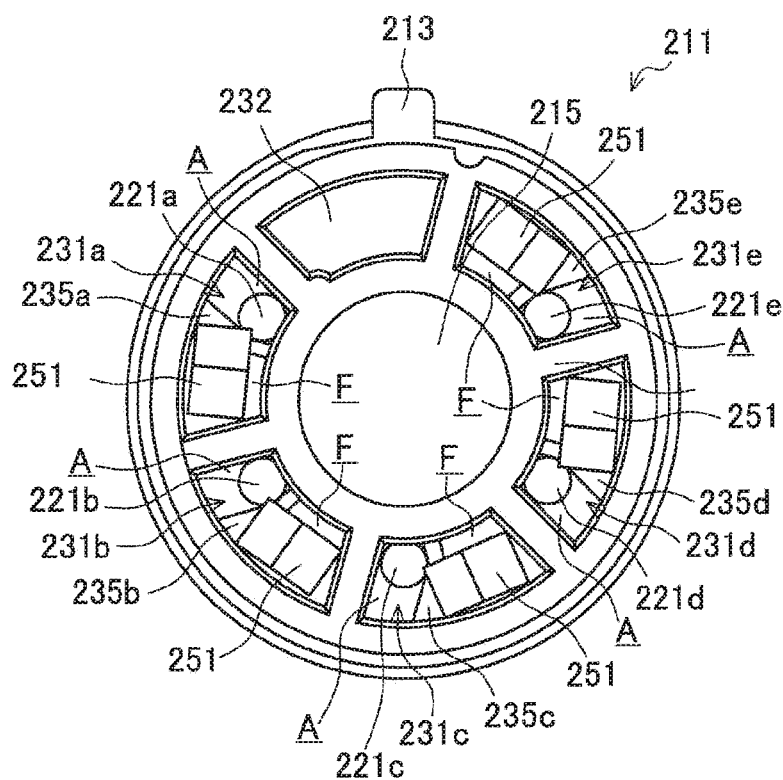
FIG. 19 illustrates the first case body containing a perfume retainer as viewed in the axial direction.
Figure 20:
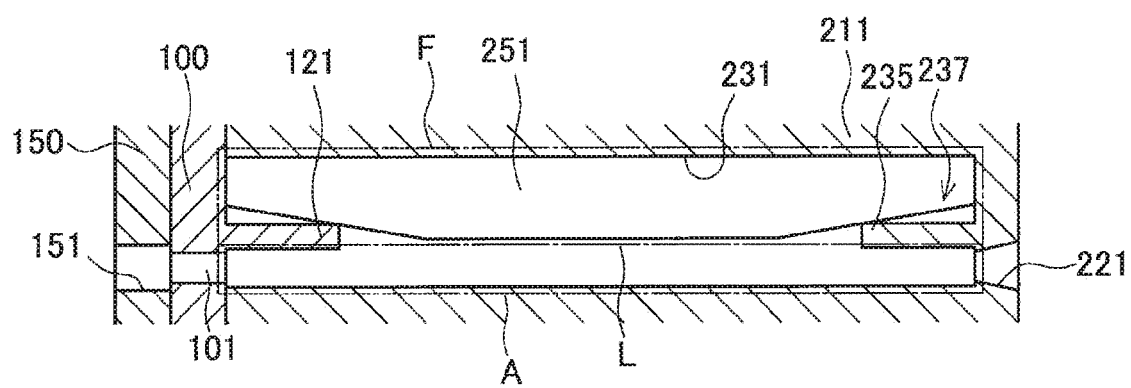
FIG. 20 is a sectional view illustrating a configuration example of a retaining space.

FIGS. 19 and 20 are views for describing the ventilation area A and the retaining area F in the retaining space 231. FIG. 19 illustrates the first case body 211 with the perfume retainer 251 arranged in the retaining space 231 as viewed from the front side. FIG. 20 is an axial sectional view schematically illustrating the retaining space 231 in which the perfume retainer 251 is arranged.

When the perfume cartridge 200 is viewed in the axial direction, the second rib 121 of the second case body 100 and the first rib 235 of the first case body 211 are arranged at a position so as to overlap each other. In FIG. 20, a space above an imaginary line L connecting the two ribs 121 and 235 is the retaining area F in which the perfume retainer 251 is arranged, and a space below the imaginary line L is the ventilation area A that can face the first opening 221 and the second opening 151 of the case cover 150. The ventilation area A linearly connects the first opening 221 and the second opening 151 along the axial direction. Thus, the ventilation resistance of air that is supplied from the first opening 221 into the retaining space 231 and flows via the communication hole 101 to the second opening 151 is lowered.

The retaining area F is arranged adjacent to the ventilation area A in a direction intersecting the axial direction. The retaining area F and the ventilation area A communicate with each other via the space between the two ribs 121 and 235. A central portion in the axial direction of the perfume retainer 251 arranged in the retaining area F is arranged in the space between the two ribs 121 and 235 and arranged close to the ventilation area A. This arrangement facilitates vaporization of liquid perfume retained by the perfume retainer 251 by a flow of air that passes through the ventilation area A. At this time, in a case where the perfume retainer 251 is in the form of an impregnation material impregnated with liquid perfume, the liquid perfume penetrates to a portion positioned on the ventilation area A side of the impregnation material, and this facilitates continuous vaporization of the perfume.

The two ribs 121 and 235 have a function as a restricting portion that limits movement of the perfume retainer 251 toward the ventilation area A. Furthermore, in the present embodiment, it can also be said that a recess 237 that is formed by the first rib 235 in the retaining space 231 in the first case body 211 and contains an end portion of the perfume retainer 251 has a function as the restricting portion.

The perfume cartridge 200 according to the present embodiment has, on a side surface of the perfume retainer 251 arranged in the retaining area F, the ventilation area A through which air passes. When air passes through the ventilation area A, the liquid perfume is vaporized, mixed with the air, and released. At this time, movement of the perfume retainer 251 toward the ventilation area A is limited. Consequently, an increase in ventilation resistance of air that passes through the ventilation area A is prevented. Furthermore, a space from the first opening 221, which is an air supply port, to the second opening 151, which is a release port, is a closed space without any other open ports. With this arrangement, the perfume vaporized by ventilation can be efficiently released from the release port.

<3. Configuration Example of Scent Providing Device>

So far, the configuration example of the perfume cartridge 200 as the perfume retaining structure according to the present embodiment has been described. Next, a configuration example of the scent providing device 1 that is used with the perfume cartridge 200 fitted will be described.

(3.1 Example of Overall Configuration)

As illustrated in FIGS. 1 and 2, the scent providing device 1 includes the perfume cartridge 200 and the device main body 700. In addition to the battery 810, the circuit board 820, and the air pump 840 included in the housing 710, the device main body 700 includes, on the front end side of the housing 710, a prism portion 500, a rotation operation portion 600, and a base portion 740.

Figure 21:
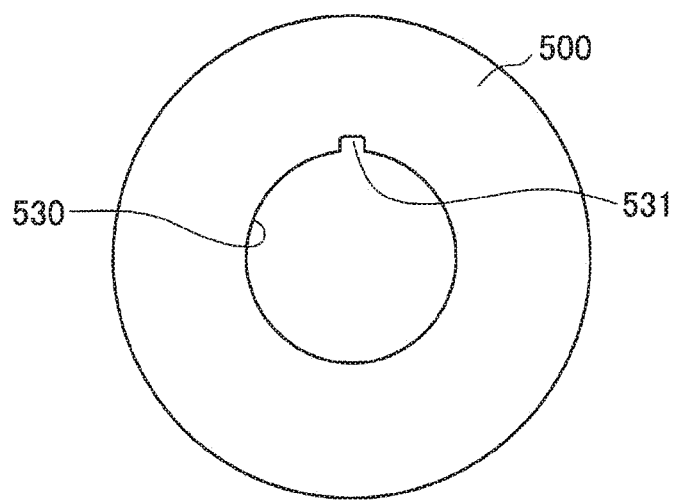
FIG. 21 is a front view of a prism body of the perfume retaining structure according to the same embodiment as viewed in the axial direction.
Figure 22:
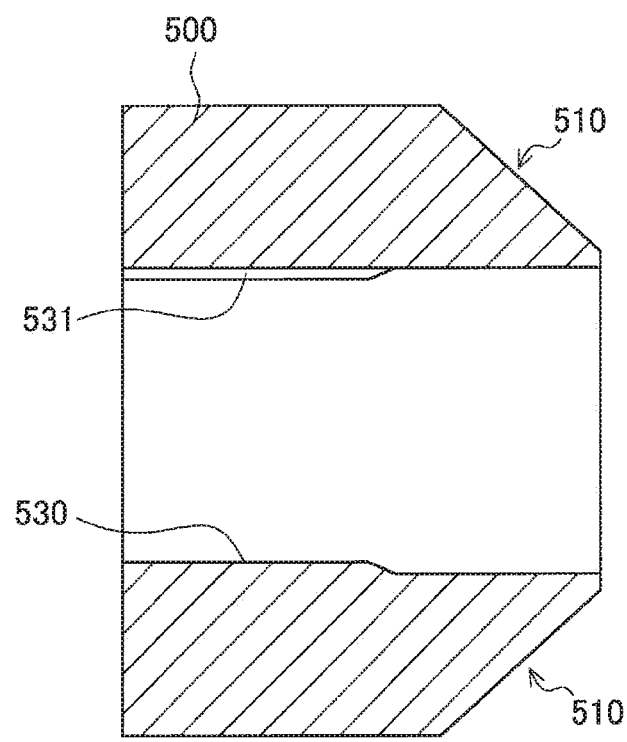
FIG. 22 is an axial sectional view of the prism body of the perfume retaining structure according to the same embodiment.

The prism portion 500 includes a transparent material, and is arranged in the rotation operation portion 600. The prism portion 500 may be press-fitted into the rotation operation portion 600, or may be joined or fixed by appropriate means. FIGS. 21 and 22 are explanatory views illustrating a configuration example of the prism portion 500. FIG. 21 is a front view of the prism portion 500 as viewed in the axial direction. FIG. 22 is an axial sectional view of the prism portion 500.

The prism portion 500 has an axial hole 530 in which the perfume cartridge 200 is arranged. A positioning groove 531 that serves as a positioning element for fitting the perfume cartridge 200 is formed on a part of the outer peripheral surface of the axial hole 530. The prism portion 500 has, on the rear side, a tapered shape having a diameter that gradually decreases toward a rear end portion. The outer surface of the tapered shape portion is mirror-finished to serve as a mirror surface portion 510. Thus, a user can visually identify, from the front side of the scent providing device 1 via the prism portion 500, characters, designs, and the like on the outer peripheral surface of the perfume cartridge 200 reflected on the mirror surface portion 510. A constituent material of the prism portion 500 is not particularly limited, as long as it has transparency after formation. For example, the prism portion 500 may be constituted by glass, crystal, or transparent resin.

Returning to FIGS. 1 and 2, the rotation operation portion 600 is arranged on the outer periphery of the prism portion 500 and the perfume cartridge 200. The rotation operation portion 600 has an integrated outer cylinder portion 610 and a retaining portion 620. The outer cylinder portion 610 has an axial hole 611 in which the prism portion 500 is fitted, and is arranged on the outer periphery of the prism portion 500. The retaining portion 620 has a spindle-shaped portion 630 that has a tapered shape having a diameter that gradually increases toward the front side, and an inner cylinder portion 640 disposed continuously with a rear end portion of the spindle-shaped portion 630. The spindle-shaped portion 630 is arranged on the outer periphery of the mirror surface portion 510 of the prism portion 500, and the inner cylinder portion 640 retains the perfume cartridge 200 in an inner peripheral portion. On the inner peripheral portion of the inner cylinder portion 640, a positioning groove 641 is formed and arranged continuously with the positioning groove 531 of the prism portion 500.

The case 210 of the perfume cartridge 200 is provided with the protrusion 212 that serves as a positioning element for fitting the perfume cartridge 200. The protrusion 212 is fitted in the positioning groove 531 on the prism portion 500 and the positioning groove 641 on the inner cylinder portion 640. Therefore, the perfume cartridge 200 can be positioned with respect to the rotation operation portion 600, and the rotation operation portion 600 and the case 210 of the perfume cartridge 200 can be rotated together.

The base portion 740 has a support portion 750 and a platform portion 760. The support portion 750 has a tubular shape. The platform portion 760 is supported in an inner peripheral portion of the support portion 750 so as to be movable in the axial direction. The platform portion 760 and the support portion 750 are coupled by a heart cam mechanism 763. The platform portion 760 can be retained at an advanced position as well as at a retracted position with respect to the support portion 750. Furthermore, a rear end portion of the perfume cartridge 200 is rotatably supported in the inner peripheral portion of the support portion 750. Moreover, the inner cylinder portion 640 of the retaining portion 620 of the rotation operation portion 600 is rotatably supported on the front side of the inner peripheral portion of the support portion 750.

The support portion 750 is provided with a piston 855 as an engagement element that can enter a recess 217 disposed on the outer peripheral surface of the rear end portion of the perfume cartridge 200. The piston 855 is biased toward the outer peripheral surface of the perfume cartridge 200 by a piston spring 853. Therefore, while the perfume cartridge 200 is being rotated, the piston spring 853 contracts and the piston 855 retracts. When one of the recesses 217 coincides with the position of the piston 855, the piston 855 enters the recess 217. Therefore, it is possible to fix the perfume cartridge 200 to a predetermined rotation position, and give a user a rotational operation feeling.

The platform portion 760 has a fixed axle 761 that extends toward the front side. The fixed axle 761 is inserted into the cylindrical portion 155 of the case cover 150 of the perfume cartridge 200. The engagement portion (not illustrated) (the portion indicated by reference numeral 769 in FIGS. 26 and 27) is disposed at a front end of the fixed axle 761. In the cylindrical portion 155 of the case cover 150 of the perfume cartridge 200, the engagement portion engages with an engagement portion (not illustrated) formed in the cylindrical portion 155 to restrict relative rotation between the case cover 150 and the base portion 740. Therefore, the rotation operation portion 600 and the case 210 of the perfume cartridge 200, which can rotate together, can rotate relative to the base portion 740.

The platform portion 760 has an air supply port 765 that penetrates the platform portion 760 in the axial direction. The air pump 840 is driven by power supplied from the battery 810 to introduce air into the air supply port 765. The air introduced into the air supply port 765 is supplied to one of the plurality of retaining spaces 231 disposed in the perfume cartridge 200.

Furthermore, the platform portion 760 has a protrusion 764 for positioning. The protrusion 764 can be engaged with a locking groove (not illustrated) (a portion indicated by reference numeral 643 in FIG. 27) formed on the inner cylinder portion 640 of the rotation operation portion 600. Specifically, the protrusion 764 of the platform portion 760 engages with the locking groove on the inner cylinder portion 640 of the rotation operation portion 600 in a state where the platform portion 760 is retained by the support portion 750 at the advanced position. Furthermore, in a state where the platform portion 760 is retained by the support portion 750 at the retracted position, the protrusion 764 of the platform portion 760 is disengaged from the locking groove on the inner cylinder portion 640. Such a mechanism functions as a rotation lock mechanism that limits relative rotation between the rotation operation portion 600 and the base portion 740 in a state where the perfume cartridge 200 has been removed from the scent providing device 1. The rotation lock mechanism will be described later in detail.

The air pump 840 may be, for example, a diaphragm pump that sucks and pumps air by deforming the diaphragm by supply of an alternating current to a piezoelectric element. The battery 810 may be a replaceable cell that only discharges, or may be a secondary cell that can charge and discharge. Driving of the air pump 840 is controlled by operating an operation switch 730. For example, the operation switch 730 is pressed to turn on or off a switching element of the circuit board 820, and power is supplied from the battery 810 to the air pump 840. Therefore, air is supplied to the perfume cartridge 200 via the air supply port 765.

For example, energization may be switched between on and off every time the operation switch 730 is repeatedly pressed, or the energization may remain on while the operation switch 730 is being pressed. Another electronic component as exemplified by a light source such as a light emitting diode (LED) that indicates an actuation state of the scent providing device 1 may be installed on the circuit board 820. Furthermore, a communication interface may be installed on the circuit board 820 so that the scent providing device 1 can be operated by using a remote controller, a smart phone, or the like.

Note that the air blowing source that supplies air toward the perfume cartridge 200 is not limited to the air pump 840, and may be, for example, a blower of a type having a rotating fan. Furthermore, the air blowing source that supplies air toward the perfume cartridge 200 may not be of an electrically-driven type but of a manually-operated type. In a case of where the air blowing source is of a manually-operated type, the battery, the operation switch, and the circuit board may be omitted.

Figure 23:
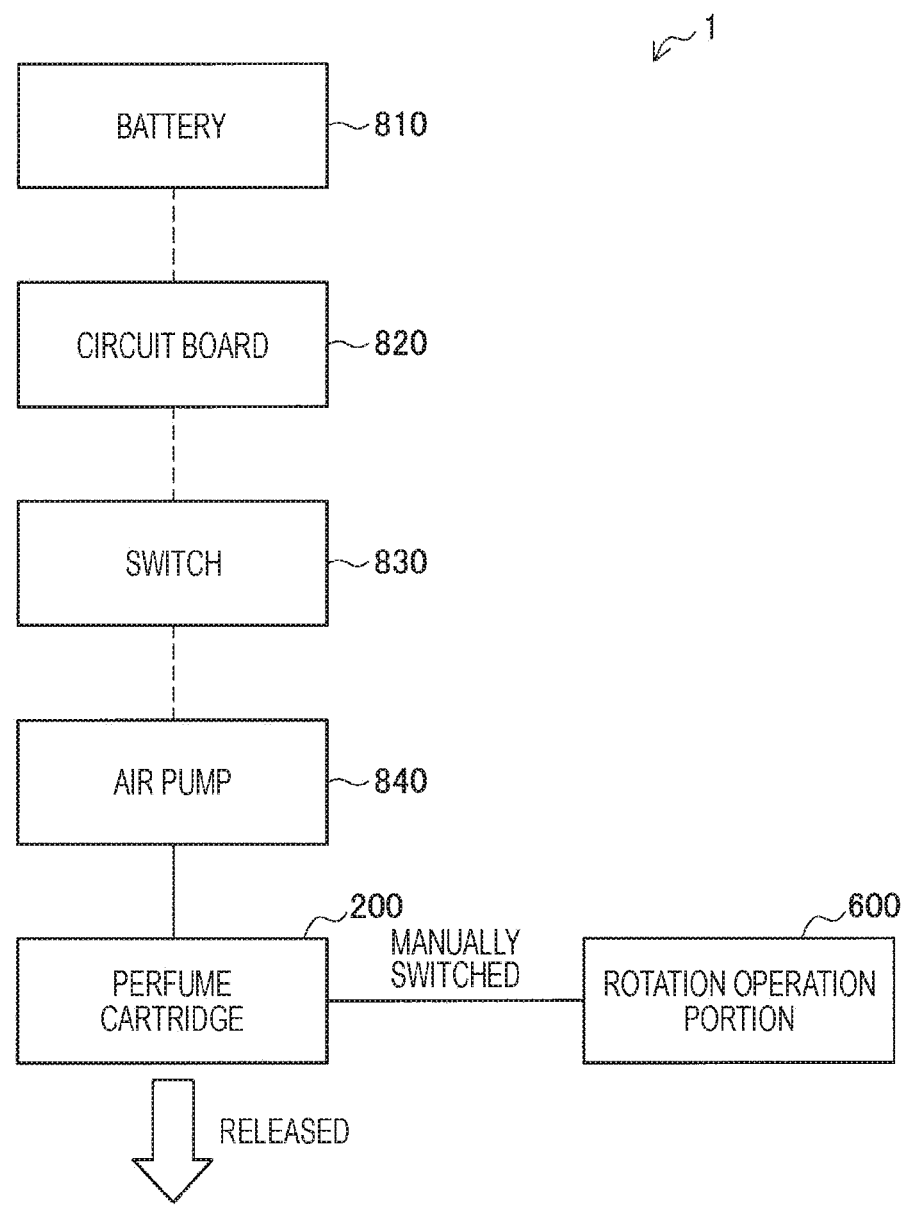
FIG. 23 is a block diagram illustrating an example of a system configuration of the scent providing device.
Figure 24:
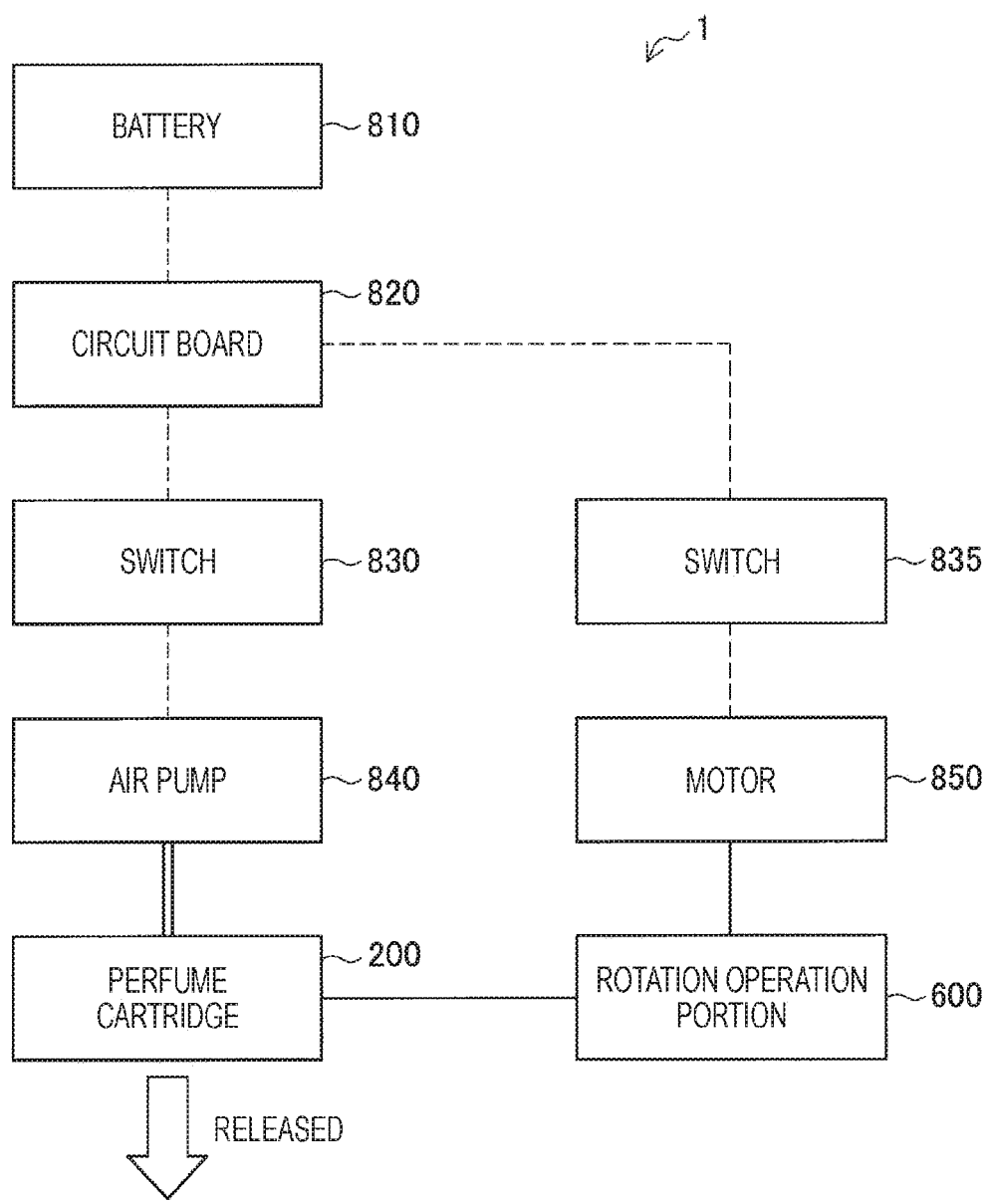
FIG. 24 is a block diagram illustrating another example of the system configuration of the scent providing device.

FIGS. 23 and 24 are block diagrams illustrating examples of a system configuration of the scent providing device 1. In the examples of FIGS. 23 and 24, the battery 810 is electrically connected to the air pump 840 via the circuit board 820 and a switching element 830. In response to an operation on the operation switch 730, power of the battery 810 is supplied to the air pump 840. When the air pump 840 is driven and air is supplied to the retaining space 231 in the perfume cartridge 200, liquid perfume retained by the perfume retainer arranged in the retaining space 231 vaporizes, and a scent is released together with the air. In the example of FIG. 23, the rotation operation portion 600 can be manually rotated to switch which retaining space 231 in the perfume cartridge 200 should be the retaining space 231 into which air supplied from the air pump 840 is to be introduced.

Furthermore, in the example of FIG. 24, the battery 810 is electrically connected, via the circuit board 820 and a switching element 835, to a motor 850 that drives the rotation operation portion 600 to rotate. For example, in response to an operation on a rotation changeover switch by a user, power of the battery 810 is supplied to the motor 850, and the rotation operation portion 600 is driven to rotate. It may thus be possible to switch which retaining space 231 in the perfume cartridge 200 should be the retaining space 231 into which air supplied from the air pump 840 is to be introduced.

(3.2. Rotation Operation)

Next, rotation operation of the perfume cartridge 200 in the scent providing device 1 will be described with reference to FIGS. 2 and 25. FIG. 2 illustrates a state in which the scent providing device 1 is not in use, and FIG. 25 illustrates a state in which the scent providing device 1 is in use.

As illustrated in FIG. 2, when the scent providing device 1 is not in use, the retaining spaces 231 in the perfume cartridge 200 do not communicate with the air supply port 765, and the pseudo space 232 is aligned with an outlet of the air supply port 765. Since the second opening 151 of the case cover 150 is positioned in the same phase with the air supply port 765, the pseudo space 232 is aligned with the second opening 151. Therefore, none of the retaining spaces 231 in which the perfume retainers 251 are arranged communicate with the air supply port 765 and the second opening 151, and this state prevents releasing of the scent.

Figure 25:
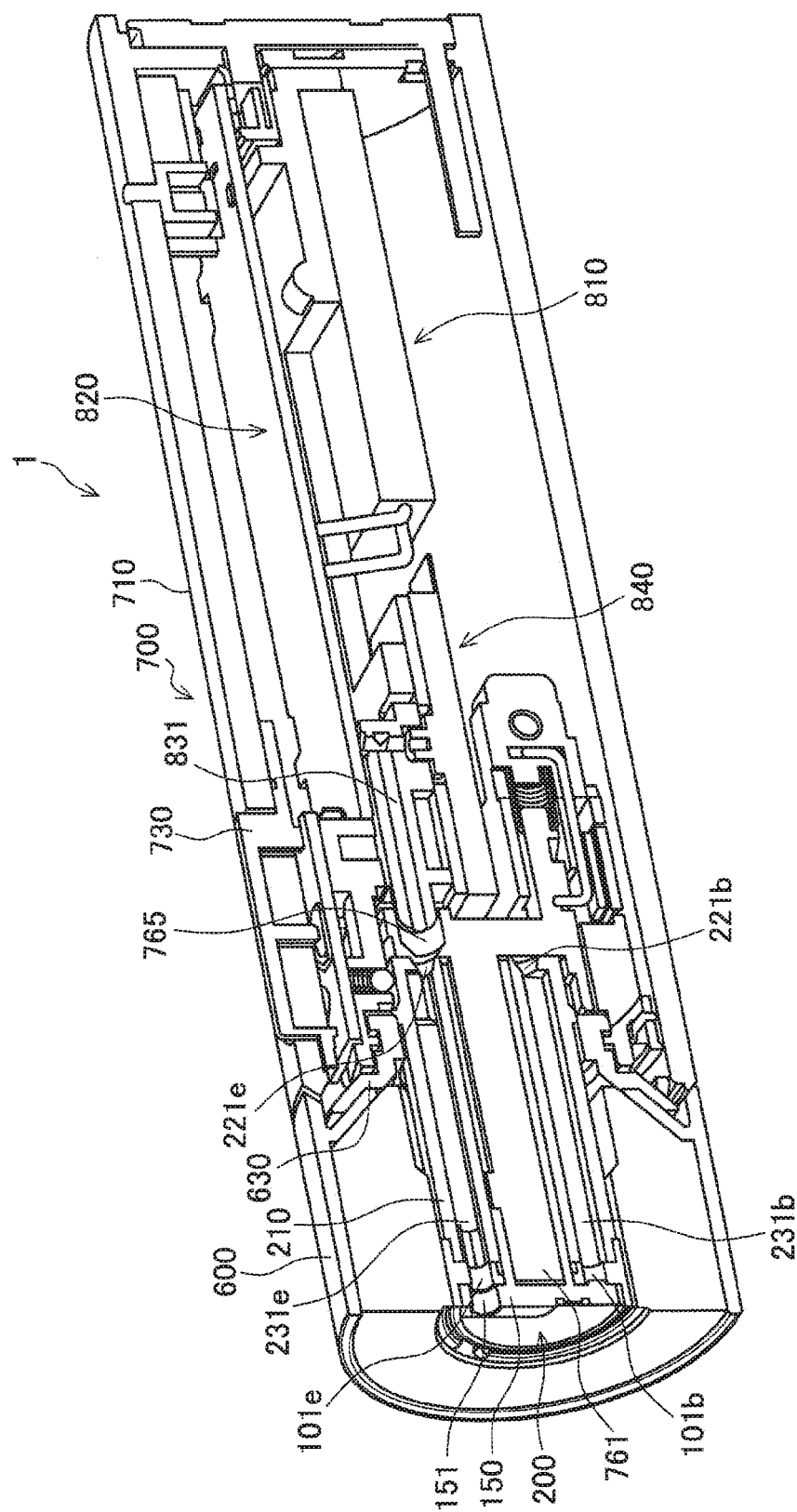
FIG. 25 is a perspective view of an axial cross section of the scent providing device according to the same embodiment.

As illustrated in FIG. 25, when the scent providing device 1 is in use, the rotation operation portion 600 is rotated to cause the perfume cartridge 200 to rotate together and allow the desired retaining space 231e to communicate with the air supply port 765 via the first opening 221e. At this time, the retaining space 231e that communicates with the air supply port 765 communicates with the second opening 151 via the communication hole 101e. A user can operate the operation switch 730 to supply air from the air pump 840 to the retaining space 231e so that the liquid perfume retained by the perfume retainer 251 (not illustrated) arranged in the retaining space 231e may be vaporized and released together with the air.

(3.3. Rotation Lock Mechanism)

Figure 26:
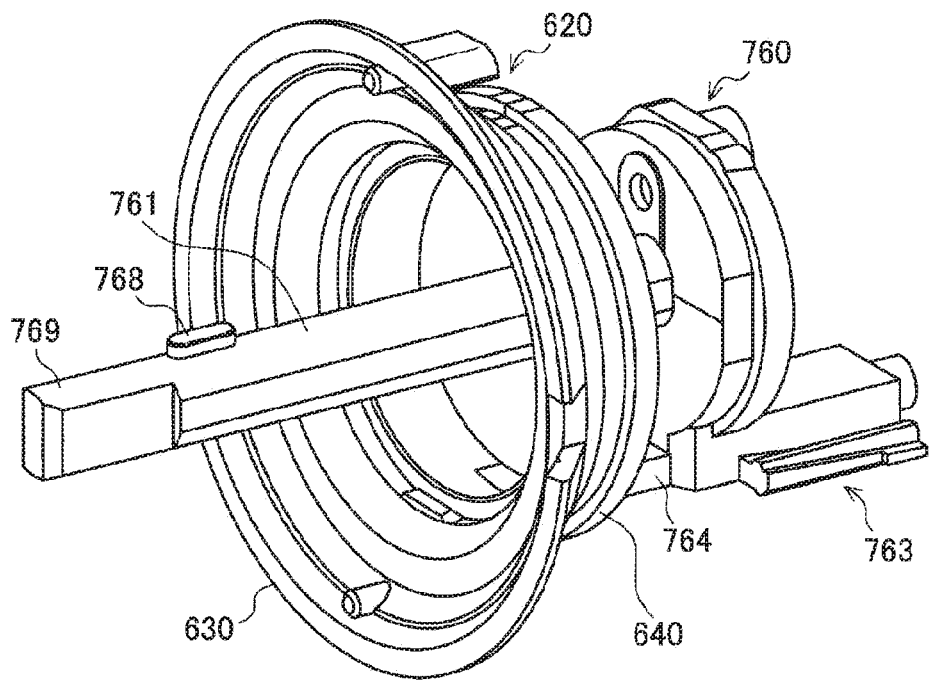
FIG. 26 is an explanatory view illustrating a rotation lock mechanism of the scent providing device according to the same embodiment.
Figure 27:
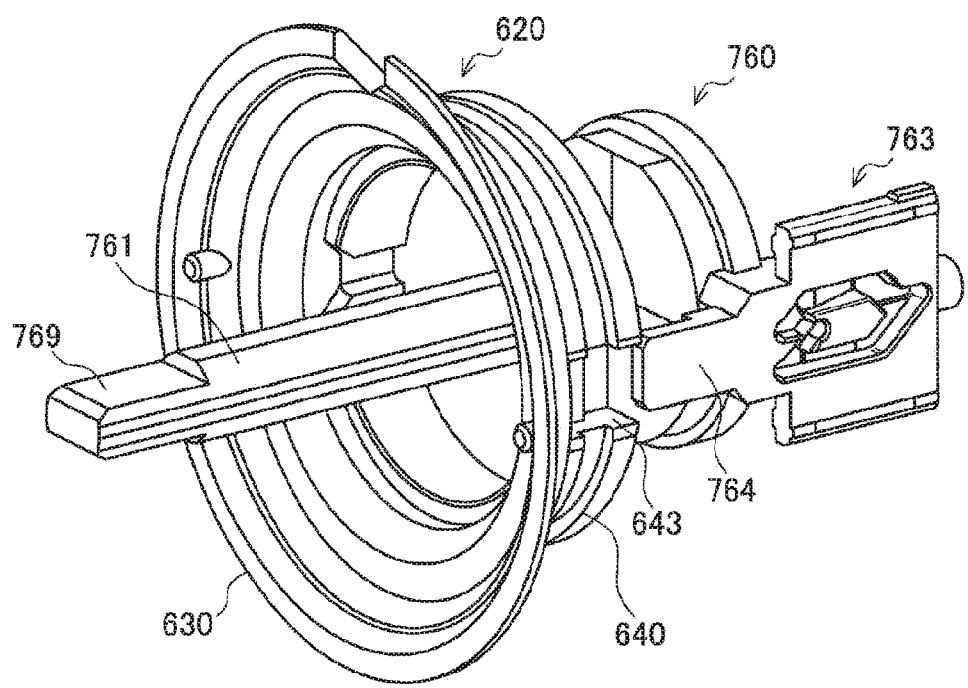
FIG. 27 is an explanatory view illustrating operation of the rotation lock mechanism of the scent providing device according to the same embodiment.

Next, the rotation lock mechanism of the scent providing device 1 will be described with reference to FIGS. 26 and 27. FIGS. 26 and 27 are perspective views illustrating only the retaining portion 620 of the rotation operation portion 600 and the platform portion 760 of the base portion 740. FIG. 27 illustrates a state of the retaining portion 620 and the platform portion 760 relatively rotated by 90 degrees from the state in FIG. 26.

As described above, the positioning groove 641 is formed on the inner peripheral portion of the inner cylinder portion 640 of the retaining portion 620. An engagement groove 643 is formed on an outer peripheral portion of the inner cylinder portion 640, at a position rotated 180 degrees from the position where the positioning groove 641 is disposed. The engagement groove 643 can be engaged with the protrusion 764 disposed on the platform portion 760 of the base portion 740. As described above, the platform portion 760 of the base portion 740 is supported by the heart cam mechanism 763 so as to allow the platform portion 760 to move in the axial direction in the inner peripheral portion of the support portion 750. In a state where the platform portion 760 has moved toward the front side, the protrusion 764 of the platform portion 760 enters and engages with the engagement groove 643 on the retaining portion 620. In a state where the platform portion 760 has moved toward the rear side, the protrusion 764 and the engagement groove 643 are disengaged from each other. FIGS. 26 and 27 illustrate a state where the platform portion 760 has moved toward the rear side and the protrusion 764 and the engagement groove 643 are disengaged from each other.

Figure 28:
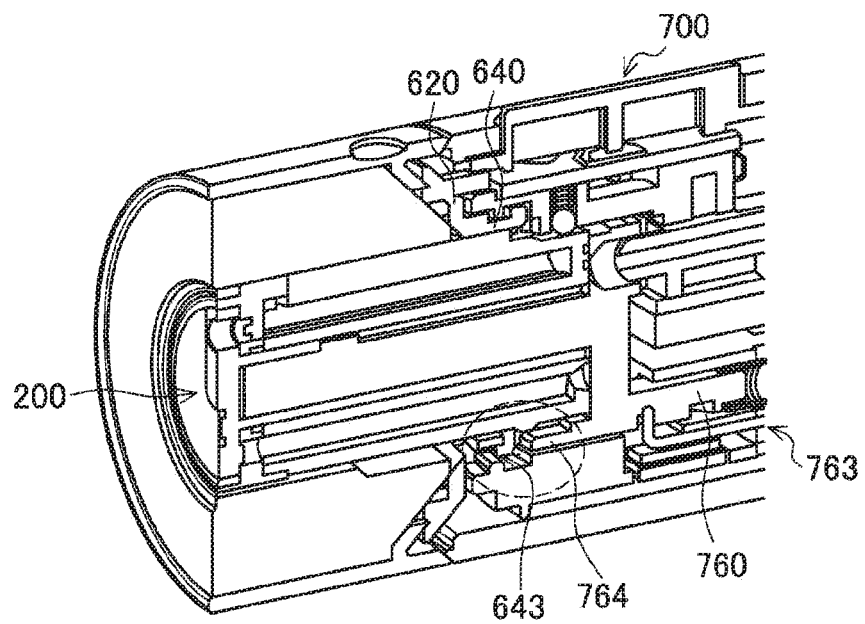
FIG. 28 is an explanatory view illustrating the operation of the rotation lock mechanism of the scent providing device according to the same embodiment.
Figure 28:
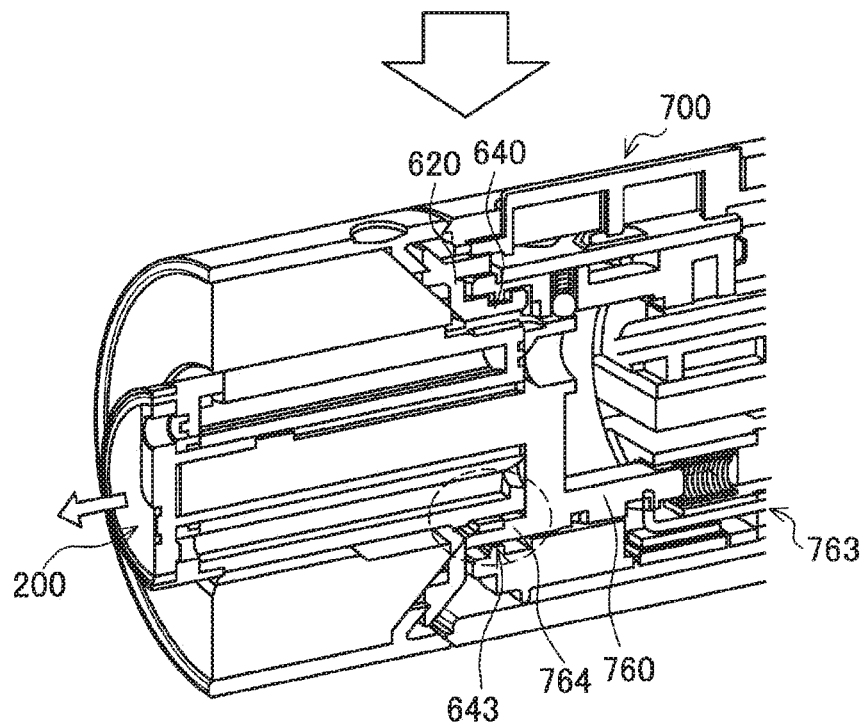
Figure 29:
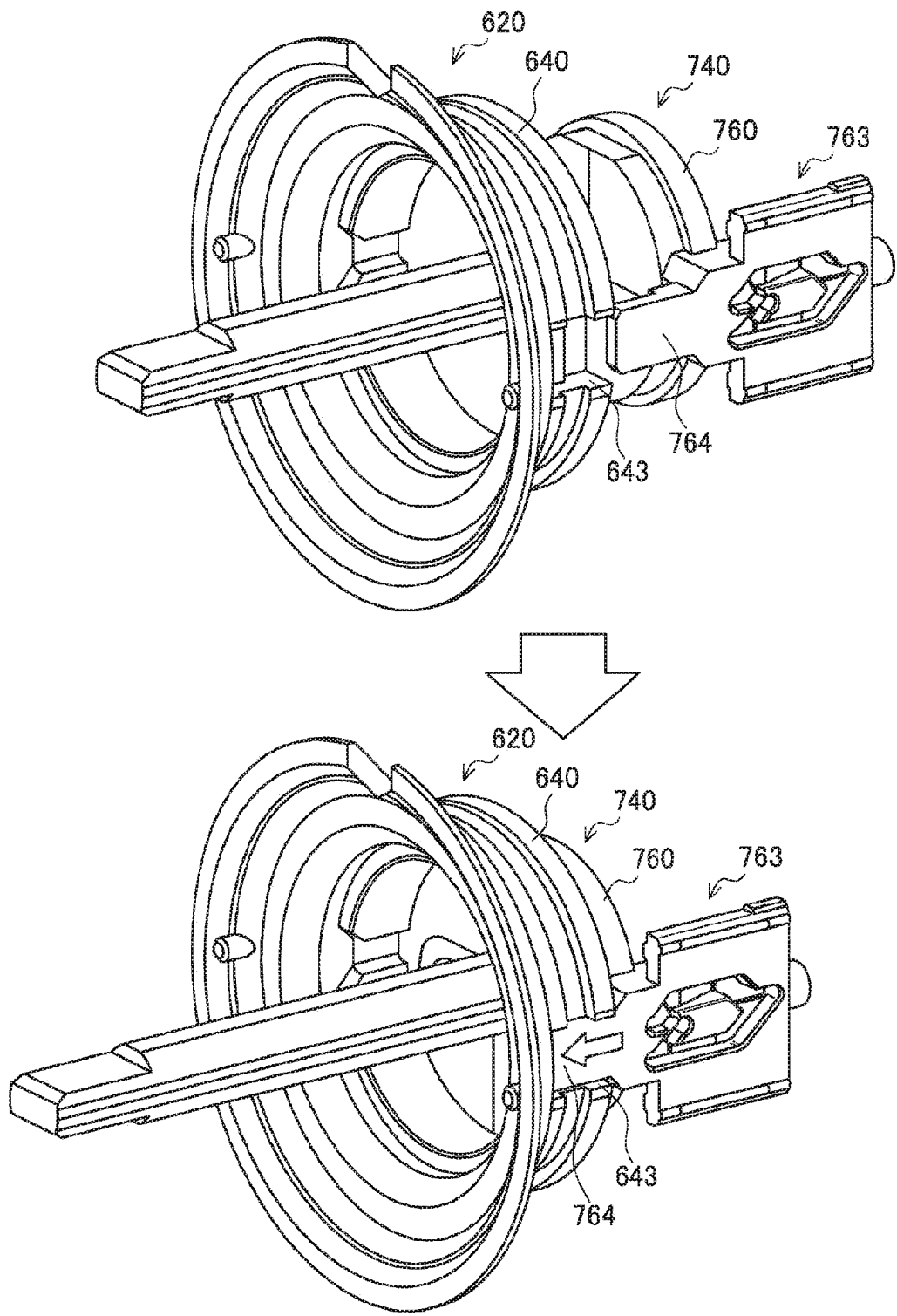
FIG. 29 is an explanatory view illustrating the operation of the rotation lock mechanism of the scent providing device according to the same embodiment.

Operation of the rotation lock mechanism will be specifically described with reference to FIGS. 28 and 29. FIG. 28 is an axial sectional view of a front end portion of the scent providing device 1. FIG. 29 is a perspective view illustrating only the retaining portion 620 of the rotation operation portion 600 and the platform portion 760 of the base portion 740, and illustrates a perspective view of the retaining portion 620 and the platform portion 760 illustrated in FIG. 28 as viewed from below. In each of FIGS. 28 and 29, a state where the perfume cartridge 200 is fitted in the device main body 700 is illustrated in an upper part, and a state where the perfume cartridge 200 is being removed from the device main body 700 is illustrated in a lower part.

As illustrated in the upper parts of FIGS. 28 and 29, in a state where the perfume cartridge 200 is fitted in the device main body 700, the heart cam mechanism 763 retains the platform portion 760 at the retracted position. At this time, the protrusion 764 of the platform portion 760 and the engagement groove 643 on the inner cylinder portion 640 of the retaining portion 620 are disengaged from each other. Thus, the retaining portion 620 can now rotate relative to the platform portion 760, and the perfume cartridge 200 that rotates together with the rotation operation portion 600 can now rotate with respect to the device main body 700.

On the other hand, as illustrated in the lower parts of FIGS. 28 and 29, when the perfume cartridge 200 is removed from the device main body 700, the heart cam mechanism 763 retains the platform portion 760 at the advanced position. At this time, the protrusion 764 of the platform portion 760 is engaged with the engagement groove 643 on the inner cylinder portion 640 of the retaining portion 620. Thus, the retaining portion 620 and the platform portion 760 are now unable to rotate relative to each other, and the retaining portion 620 is retained at a prearranged rotation position when the perfume cartridge 200 is attached or detached. Therefore, the perfume cartridge 200 can be easily attached to or detached from the device main body 700 by aligning the perfume cartridge 200 with the predetermined rotation position.

(3.4. Rotation Restricting Mechanism)

Next, a rotation restricting mechanism for the case 210 and the case cover 150 of the perfume cartridge 200 will be described. The perfume cartridge 200 according to the present embodiment has the rotation restricting mechanism that limits relative rotation between the case 210 and the case cover 150 in a state where the perfume cartridge 200 is not fitted in the device main body 700.

In the axial sectional view of the perfume cartridge 200 illustrated in FIG. 6, the engagement protrusion 159 formed on the rear end surface of the disk portion 153 of the case cover 150 has entered the communication hole 101c in the second case body 100. In this state, rotation of the case cover 150 with respect to the case 210 is limited.

Figure 30:
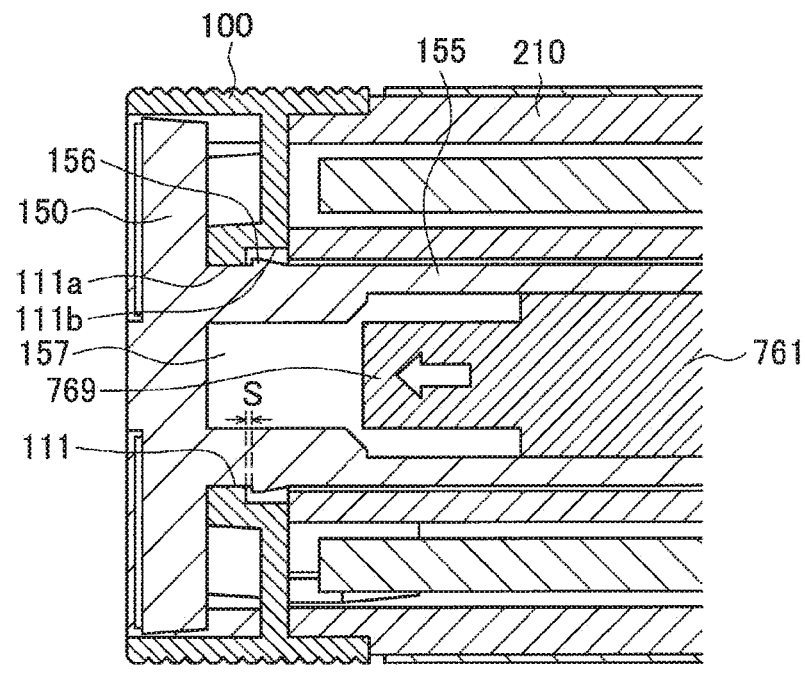
FIG. 30 is an explanatory view illustrating operation of a rotation restricting mechanism of the perfume retaining structure according to the same embodiment.
Figure 30:
Figure 30:
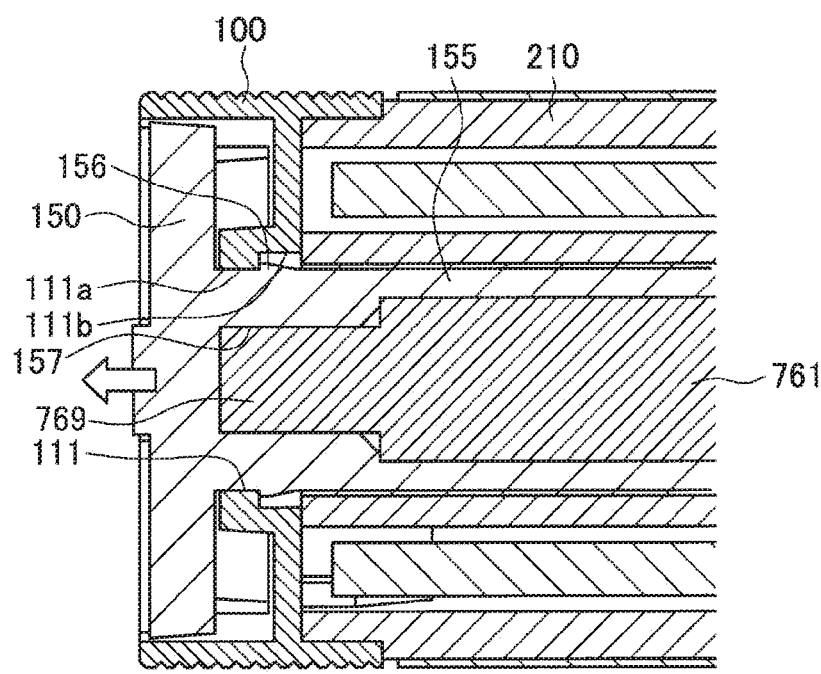

FIG. 30 is a view for describing operation of the rotation restricting mechanism when the perfume cartridge 200 is fitted in the device main body 700. As described above, in a state where the case cover 150 and the case 210 are assembled, the locking claws 156 disposed on an outer peripheral portion of the cylindrical portion 155 of the case cover 150 are locked to the step portion between the small-diameter portion 111a and the large-diameter portion 111b of the axial hole 111 disposed on the second case body 100. At this time, a gap S that is at least equal to or larger than the height of the engagement protrusion 159 is formed between the locking claws 156 and the step portion (see the view illustrated in an upper part of FIG. 30).

When the perfume cartridge 200 is fitted, the engagement portion 769 disposed at the front end of the fixed axle 761 of the platform portion 760 is inserted into the engagement recess 157 disposed in the bottom portion of the internal space in the cylindrical portion 155 of the case cover 150. At this time, for example, the engagement portion 769 is lightly press-fitted into the engagement recess 157, and the case cover 150 moves toward the front by the length of the gap S described above. As a result, the engagement protrusion 159 of the case cover 150 illustrated in FIG. 6 moves to a position nearer to the front than the communication hole 101c, and the case cover 150 can now rotate with respect to the case 210. Therefore, the case 210 can rotate in a state where the perfume cartridge 200 is fitted in the device main body 700.

With the rotation restricting mechanism like this, when the perfume cartridge 200 is not in use, the rotation position of the second opening 151 of the case cover 150 is aligned with the position where the pseudo space 232 is arranged in the case 210 to ensure that none of the retaining spaces 231 in which the perfume retainers 251 are arranged are opened to the outside via the second opening 151. Thus, leakage of the perfume can be prevented when the perfume cartridge 200 is not in use.

Note that the engagement protrusion 159 and the communication hole 101 that constitute the rotation restricting mechanism are an example of an engagement portion and an engaged portion, and the engagement portion and the engaged portion are not limited to such an example. The engagement portion and the engaged portion are only required to be engaged before the perfume cartridge 200 is fitted in the device main body 700 and disengaged from each other after the perfume cartridge 200 has been fitted in the device main body 700.

<4. Method of Manufacturing Perfume Cartridge (Perfume Retaining Structure)>

Figure 31:
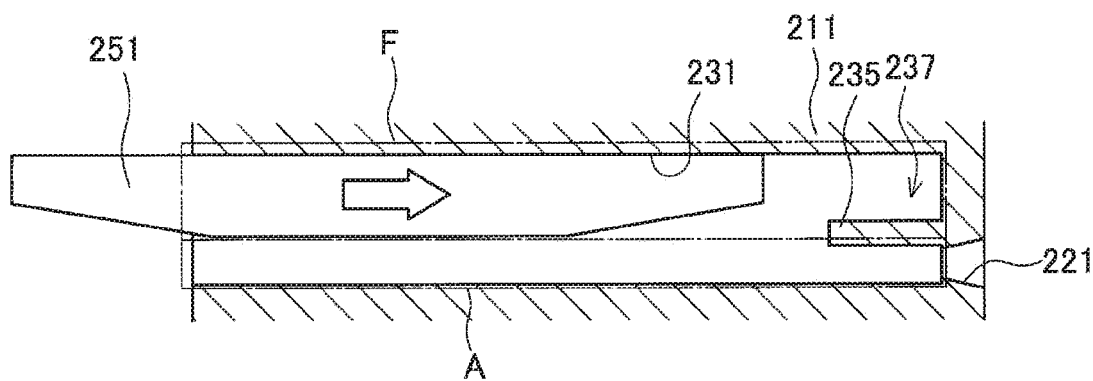
FIG. 31 is an explanatory view illustrating a second step of a perfume cartridge manufacturing method according to the same embodiment.
Figure 32:
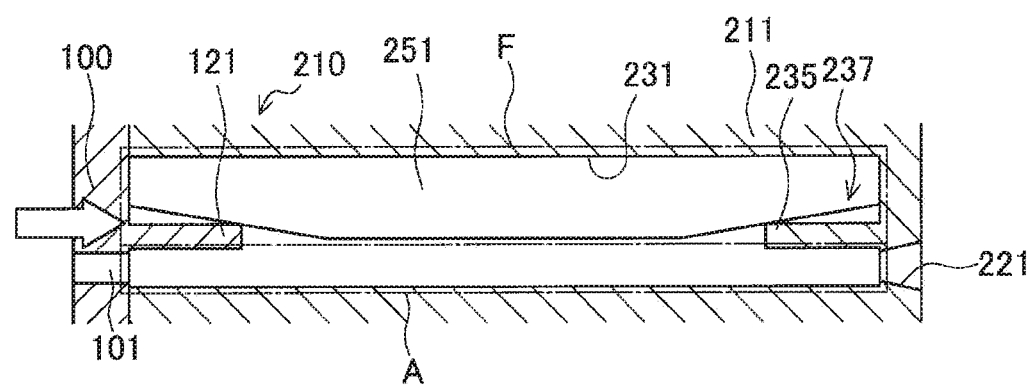
FIG. 32 is an explanatory view illustrating a third step of the perfume cartridge manufacturing method according to the same embodiment.
Figure 33:
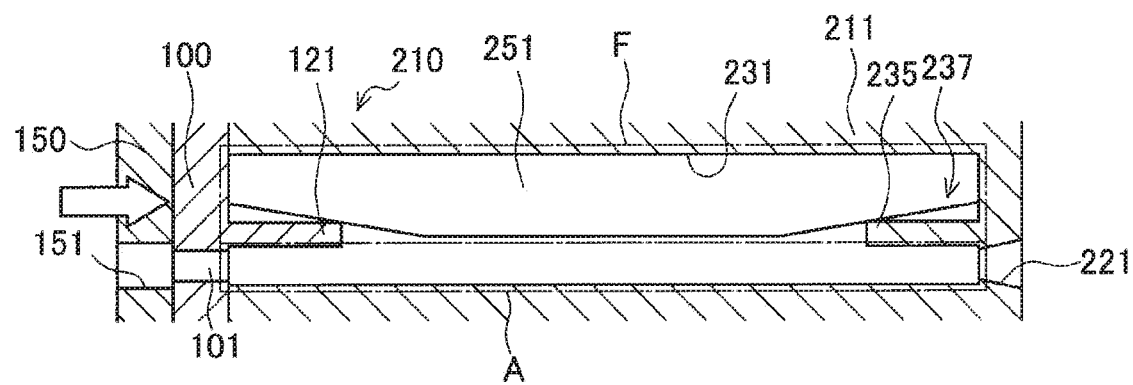
FIG. 33 is an explanatory view illustrating a fourth step of the perfume cartridge manufacturing method according to the same embodiment.

Next, an example of a method of manufacturing the perfume cartridge 200 according to the present embodiment illustrated in FIGS. 3 to 6 will be described. The method of manufacturing the perfume cartridge 200 according to the present embodiment includes first to fourth steps. The method of manufacturing the perfume cartridge 200 will be described below in order of steps with reference to FIGS. 31 to 33 FIGS. 31 to 33 are schematic views illustrating a vicinity of one of the plurality of retaining spaces 231 constituting the perfume cartridge 200.

(4.1. First Step)

In the first step, the first case body 211 exemplified in FIGS. 8 to 10 and the like is produced. In the first case body 211, the plurality of retaining spaces 231 and the pseudo space 232 are formed. The first rib 235 is formed on the rear end side of each retaining space 231 to divide the retaining space 231 into the ventilation area A in which the first opening 221 is disposed, and the retaining area F that is arranged adjacent to the ventilation area A and communicates with the ventilation area A. The method of producing the first case body 211 is not particularly limited. For example, the first case body 211 may be molded by pouring a molten resin material into a mold and solidifying the resin material. The resin material used is not particularly limited, but is preferably a resin material having resistance to liquid perfume.

(4.2. Second Step)

In the second step, the perfume retainer 251 is stored in the retaining area F in the first case body 211. For example, as illustrated in FIG. 31, each perfume retainer 251 that already retains liquid perfume is inserted into the retaining area F in the corresponding retaining space 231. At this time, a rear end portion of the perfume retainer 251 is inserted into the recess 237 formed by the first rib 235. Liquid perfumes retained by the perfume retainers 251 contained in the corresponding retaining spaces 231 may be all the same, or some or all of the liquid perfumes may be different from each other.

Note that, in the second step, it is also possible to insert, into the retaining area F, an impregnation material that does not retain liquid perfume, and then apply liquid perfume to impregnate the impregnation material with the liquid perfume.

(4.3. Third Step)

In the third step, the case 210 is produced by attaching the second case body 100 to the first case body 211 in which the perfume retainers 251 are arranged in all the retaining spaces 231. For example, as illustrated in FIG. 32, the second case body 100 has the plurality of communication holes 101 that communicates with the corresponding retaining spaces 231 in the first case body 211, and the second ribs 121 that are erected in the corresponding retaining spaces 231. By attaching the second case body 100 to the first case body 211, movement of each perfume retainer 251 toward the ventilation area A is restricted by the first rib 235 and the second rib 121.

(4.4. Fourth Step)

In the fourth step, the case cover 150 having the second opening 151 is attached to the case 210. As illustrated in FIG. 33, the case cover 150 is provided with the second opening 151, and the case cover 150 is attached to the case 210 so as to allow relative rotation with respect to each other. Thus, the rotation position of the case cover 150 with respect to the case 210 is switched to allow the second opening 151 to communicate with one of the retaining spaces 231 via the corresponding communication hole 101. Although not illustrated, at the time of manufacturing, the second opening 151 may be aligned with and attached to a position corresponding to the pseudo space 232 disposed in the first case body 211. This arrangement prevents leakage of the scent from any one of the retaining spaces 231 when the perfume cartridge 200 is not in use.

As described above, in the perfume cartridge 200 according to the present embodiment, the retaining space 231 in the perfume cartridge 200, in which the perfume retainer 251 is arranged, has the ventilation area A and the retaining area F. The ventilation area A can face the first opening 221 and the second opening 151. The retaining area F is arranged adjacent to the ventilation area A and communicates with the ventilation area A, and the perfume retainer 251 is arranged in the retaining area F. The perfume cartridge 200 like this includes, as the restricting portion that limits movement of the perfume retainer 251 toward the ventilation area A, the first rib 235, the recess 237 formed by the first rib 235, and the second rib 121. Thus, it is possible to reduce a possibility that the perfume retainer 251 enters the ventilation area A and hinders a flow of air that passes through the ventilation area A. Consequently, ventilation resistance of air that passes through the ventilation area A is reduced, and a decrease in flow rate of the scent released from the scent providing device 1 is prevented.

Furthermore, in the perfume cartridge 200 according to the present embodiment, the restricting portion is constituted by the first rib 235 and the second rib 121 formed on the first case body 211 and the second case body 100, respectively. With this arrangement, at the time of manufacturing of the perfume cartridge 200, a structure that limits movement of the perfume retainer 251 can be easily formed by appropriately arranging the perfume retainer 251 in the retaining space 231 and appropriately assembling the first case body 211 and the second case body 100. In particular, the perfume cartridge 200 according to the present embodiment includes the plurality of retaining spaces 231 in which the perfume retainers 251 are arranged. Thus, it is significant that the structure that limits movement of the perfume retainer 251 in each retaining space 231 can be easily formed by appropriately arranging the perfume retainer 251 in the retaining space 231 and appropriately assembling the first case body 211 and the second case body 100.

Furthermore, in the perfume cartridge 200 according to the present embodiment, the case cover 150 has the engagement protrusion 159 that is engaged with the communication hole 101c in the second case body 100 while the perfume cartridge 200 is not fitted in the device main body 700 and that is disengaged from the communication hole 101c in the second case body 100 while the perfume cartridge 200 is fitted in the device main body 700. With this arrangement, the retaining space 231 in which the perfume retainer 251 is arranged can be retained as a closed space when the perfume cartridge 200 is not in use, and leakage of the scent is prevented when the perfume cartridge 200 is not in use.

The preferred embodiment of the present disclosure has been described above in detail with reference to the accompanying drawings, but the technical scope of the present disclosure is not limited to such an example. It is obvious that a person having ordinary knowledge in the technical field of the present disclosure can come up with various changes and modifications within the scope of the technical idea described in the claims, and such various changes and modifications are naturally understood to belong to the technical scope of the present disclosure.

For example, in the embodiment described above, movement of the perfume retainer 251 toward the ventilation area A is limited by the first rib 235 and the second rib 121 that divide the retaining space 231 into the ventilation area A and the retaining area F. However, the technology of the present disclosure is not limited to such an example. For example, in a case where the perfume retainer 251 has adhesiveness, the perfume retainer 251 may be fixed to an inner wall of the retaining space 231, more specifically, in an area that does not face the first opening 221 and the second opening 151. Thus, movement of the perfume retainer 251 toward the ventilation area A may be limited. Even if the ventilation area A and the retaining area F are divided in this way, the ventilation resistance of air that passes through the ventilation area A is reduced, and it is possible to prevent a decrease in flow rate of the scent released from the scent providing device 1.

Furthermore, in the embodiment described above, the ventilation area A linearly connects the first opening 221 and the second opening 151 along the axial direction, and the retaining area F is arranged adjacent to the ventilation area A in a direction intersecting the axial direction. However, the technology of the present disclosure is not limited to such an example. For example, the ventilation area A may be disposed spirally or tortuously from the first opening 221 toward the second opening 151, and the retaining area F may be arranged partially or entirely adjacent to the ventilation area A so as not to hinder a flow of air in the ventilation area A. Even if the ventilation area A and the retaining area F are arranged in this way, the ventilation resistance of air that passes through the ventilation area A is reduced Thus, a decrease in flow rate of the scent released from the scent providing device 1 is prevented.

Note that the following configurations also belong to the technical scope of the present disclosure.

(1) A perfume retaining structure including:
a perfume retainer;
a retaining space in which the perfume retainer is arranged; and
a first opening and a second opening that allow the retaining space to be opened to the outside,
in which the retaining space has
a ventilation area that faces the first opening and the second opening, and
a retaining area that is arranged adjacent to the ventilation area and communicates with the ventilation area, the perfume retainer being arranged in the retaining area.

(2) The perfume retaining structure according to (1), in which the ventilation area linearly connects the first opening and the second opening along a predetermined direction, and the retaining area is arranged adjacent to the ventilation area in a direction intersecting the predetermined direction.

(3) The perfume retaining structure according to (1) or (2), further including a restricting portion that limits movement of the perfume retainer toward the ventilation area.

(4) The perfume retaining structure according to (3), in which the restricting portion is a recess that contains a part of the perfume retainer.

(5) The perfume retaining structure according to (3), in which the restricting portion is a rib that extends between the ventilation area and the retaining area.

(6) The perfume retaining structure according to any one of (1) to (5), in which the perfume retaining structure includes a plurality of the retaining spaces.

(7) The perfume retaining structure according to any one of (1) to (6), in which the perfume retaining structure includes a perfume cartridge to be fitted in a scent providing device.

(8) The perfume retaining structure according to any one of (1) to (7), further including:
a case that has the retaining space and the first opening; and
a case cover that is attached to the case and has the second opening.

(9) The perfume retaining structure according to (8), further including a restricting portion that limits movement of the perfume retainer toward the ventilation area.

(10) The perfume retaining structure according to (9), in which the restricting portion is a recess that is disposed on the case and contains a part of the perfume retainer.

(11) The perfume retaining structure according to (9), in which
the case includes a first case body that has the retaining space, and a second case body that is attached to the first case body and has a communication hole that communicates with the retaining space, and
the restricting portion is a rib that is formed on the second case body and extends into the retaining space in the first case body.

(12) The perfume retaining structure according to any one of (8) to (11), in which
the case has a plurality of the retaining spaces and the first openings,
the case cover has the second opening,
the case cover is rotatably attached to the case, and
the second opening faces one of the plurality of the retaining spaces.

(13) The perfume retaining structure according to (12), in which
the perfume retaining structure includes a perfume cartridge to be fitted in a scent providing device, and
the case cover has an engagement portion that is engaged with an engaged portion of the case while the perfume cartridge is not fitted in the scent providing device and that is disengaged from the engaged portion of the case while the perfume cartridge is fitted in the scent providing device.

(14) The perfume retaining structure according to (12) or (13), in which the retaining spaces are arranged at regular intervals around a central axis of the perfume retaining structure.

(15) A method of manufacturing a perfume retaining structure, including:
producing a first case body provided with a retaining space that has a ventilation area provided with a first opening, and a retaining area that is divided from the ventilation area by a first rib, arranged adjacent to the ventilation area, and communicates with the ventilation area;
storing a perfume retainer or a base material of the perfume retainer in the retaining area in the first case body;
producing a case by attaching, to the first case body, a second case body that has a communication hole that communicates with the retaining space in the first case body and a second rib that is erected in the retaining space in the first case body, the first rib and the second rib limiting movement of the perfume retainer toward the ventilation area; and
attaching, to the case, a case cover that has a second opening.

(16) A scent providing device including:
a perfume retaining structure that has a perfume retainer, a retaining space in which the perfume retainer is arranged, and a first opening and a second opening that allow the retaining space to be opened to the outside; and
an air blowing source that supplies air to the retaining space,
in which the retaining space has
a ventilation area that faces the first opening and the second opening, and a retaining area that is arranged adjacent to the ventilation area and communicates with the ventilation area, the perfume retainer being arranged in the retaining area.

REFERENCE SIGNS LIST

1 Scent providing device
100 Second case body
101 Communication hole
121 Second rib (restricting portion)
150 Case cover
151 Second opening
153 Disk portion
155 Cylindrical portion
159 Engagement protrusion
200 Perfume cartridge
210 Case
211 First case body
221 First opening
231 Retaining space
235 First rib (restricting portion)
237 Recess (restricting portion)
251 Perfume retainer
700 Device main body
Ventilation area A
Retaining area F

The invention claimed is:

1. A scent retaining structure comprising:
a scent retainer;
a plurality of retaining spaces each in which the scent retainer is arranged; and
a first opening and a second opening that allow the retaining spaces to be opened to outside,
wherein the retaining spaces each have
a ventilation area connecting the first opening and the second opening,
a retaining area that is arranged adjacent to the ventilation area and communicates with the ventilation area, the scent retainer being arranged in the retaining area,
wherein the retaining spaces, including the ventilation area and the retaining area, are arranged around a central axis of the scent retaining structure, and wherein the ventilation area and the retaining area are radially arranged side by side and have same distance to the central axis of the scent retaining structure,
a restricting portion that divides the retaining area and the ventilation area, wherein the restricting portion limits movement of the scent retainer toward the ventilation area, and
wherein the ventilation area is configured to form an uninterrupted channel connecting the first opening and the second opening.

2. The scent retaining structure according to claim 1, wherein the ventilation area linearly connects the first opening and the second opening along a predetermined direction, and the retaining area is arranged adjacent to the ventilation area in a direction intersecting the predetermined direction.

3. The scent retaining structure according to claim 1, wherein the restricting portion is a recess that contains a part of the scent retainer.

4. The scent retaining structure according to claim 1, wherein the restricting portion is a rib that extends between the ventilation area and the retaining area.

5. The scent retaining structure according to claim 1, wherein the scent retaining structure is a scent cartridge to be fitted in a scent providing device.

6. The scent retaining structure according to claim 1, further comprising:
a case that has the retaining spaces and the first opening; and
a case cover that is attached to the case and has the second opening.

7. The scent retaining structure according to claim 6, wherein the restricting portion is a recess that is disposed on the case and contains a part of the scent retainer.

8. The scent retaining structure according to claim 6, wherein
the case includes a first case body that has the retaining spaces, and a second case body that is attached to the first case body and has a communication hole that communicates with the retaining spaces, and
the restricting portion is a rib that is formed on the second case body and extends into the retaining spaces in the first case body.

9. The scent retaining structure according to claim 6, wherein
the case cover is rotatably attached to the case, and
the second opening faces one of the plurality of the retaining spaces.

10. The scent retaining structure according to claim 9, wherein
the scent retaining structure is a scent cartridge to be fitted in a scent providing device, and
the case cover has an engagement portion that is engaged with an engaged portion of the case while the scent cartridge is not fitted in the scent providing device and that is disengaged from the engaged portion of the case while the scent cartridge is fitted in the scent providing device.

11. The scent retaining structure according to claim 9, wherein the retaining spaces are arranged at regular intervals around the central axis of the scent retaining structure.

12. A scent providing device comprising:
a scent retaining structure that has a scent retainer, a plurality of retaining spaces each in which the scent retainer is arranged, and a first opening and a second opening that allow the retaining spaces to be opened to outside; and
an air blowing source that supplies air to the retaining spaces,
wherein the retaining spaces have
a ventilation area connecting the first opening and the second opening,
a retaining area that is arranged adjacent to the ventilation area and communicates with the ventilation area, the scent retainer being arranged in the retaining area,
wherein the retaining spaces, each including the ventilation area and the retaining area, are arranged around a central axis of the scent retaining structure, and wherein the ventilation area and the retaining area are radially arranged side by side and have same distance to the central axis of the scent retaining structure,
a restricting portion that divides the retaining area and the ventilation area, wherein the restricting portion limits movement of the scent retainer toward the ventilation area, and
wherein the ventilation area is configured to form an uninterrupted channel connecting the first opening and the second opening.

13. The scent retaining structure according to claim 1, wherein the scent retainer is configured to retain a liquid capable of providing a scent.

14. The scent retaining structure according to claim 13, wherein the liquid includes a perfume.

15. The scent retaining structure according to claim 14, wherein the perfume includes an essential oil or an essential oil diluted with ethanol.

* * * * *